(12) United States Patent
He et al.

(10) Patent No.: US 11,110,149 B2
(45) Date of Patent: Sep. 7, 2021

(54) METHOD FOR PREDICTING AND MONITORING THE EFFICACY OF LOW-DOSE IL-2 AND HYDROXYCHLOROQUINE THERAPY IN AUTOIMMUNE DISEASES AND ITS LONG-TERM USE IN AUTOIMMUNE-RELATED CONDITIONS

(71) Applicant: KSL BIOMEDICAL INC., Williamsville, NY (US)

(72) Inventors: Jing He, Beijing (CN); Zhanguo Li, Beijing (CN)

(73) Assignee: KSL BIOMEDICAL INC., Williamsville, NY (US)

( * ) Notice: Subject to any disclaimer, the term of this patent is extended or adjusted under 35 U.S.C. 154(b) by 84 days.

(21) Appl. No.: 16/794,585

(22) Filed: Feb. 19, 2020

(65) Prior Publication Data
US 2020/0261540 A1    Aug. 20, 2020

Related U.S. Application Data

(60) Provisional application No. 62/807,856, filed on Feb. 20, 2019.

(51) Int. Cl.
*A61K 38/20* (2006.01)
*A61P 29/00* (2006.01)
*A61K 31/4706* (2006.01)

(52) U.S. Cl.
CPC ...... *A61K 38/2013* (2013.01); *A61K 31/4706* (2013.01); *A61P 29/00* (2018.01)

(58) Field of Classification Search
CPC .................................................. A61K 38/2013
See application file for complete search history.

(56) References Cited

U.S. PATENT DOCUMENTS

| | | |
|---|---|---|
| 9,669,071 B2 | 6/2017 | Klatzmann et al. |
| 10,174,121 B2 | 1/2019 | Benatuil et al. |
| 10,183,061 B2 | 1/2019 | Dorothée et al. |

FOREIGN PATENT DOCUMENTS

WO    2002078624 A1    10/2002

OTHER PUBLICATIONS

Hoes et al., "EULAR evidence-based recommendations on the management of systemic glucocorticoid therapy in rheumatic diseases"; Ann Rheum Dis 2007;66:1560-1567. doi: 10.1136/ard.2007.072157.

Duru et al., "EULAR evidence-based and consensus-based recommendations on the management of medium to high-dose glucocorticoid therapy in rheumatic diseases"; Ann Rheum Dis 2013;72:1905-1913. doi:10.1136/annrheumdis-2013-203249.

Luijten et al., "The Systemic Lupis Erythematosus Responder Index (SRI); A new SLE disease activity assessment" Autoimmunity Reviews, vol. 11, Issue 5, Mar. 2012, pp. 326-329—abstract.

International Search Report for PCT/US/2020/18778, dated May 27, 2020 (2 pages).

Written Opinion of the International Searching Authority for PCT/US/2020/18778, dated May 27, 2020 (5 pages).

Struyf et al., "Natural killer cell activity in Sjogren's syndrome and systemic lupus erythematosus: stimulation with interferons and interleukin-2 and correlation with immune complexes", Annuals of Rheumatic Diseases, 1990; 49; 690-693.

Mizui et al. "Low-dose interleukin-2 as a regulatory immunotherapy for systemic lupus erythematosus", J. Xiangya Med. 2016; 1:15 (3 pages).

*Primary Examiner* — Prema M Mertz
(74) *Attorney, Agent, or Firm* — Roach Brown McCarthy & Gruber; Kevin D. McCarthy

(57) ABSTRACT

A method of inhibiting or treating systemic lupus erythematosus (SLE) and/or primary Sjögren's Syndrome (pSS) in a subject in need thereof is disclosed. The method calls for administering to the subject a therapeutically effective low-dose amount of interleukin-2 and hydroxychloroquine alone or in combination with a therapeutically effective amount of another disease-modifying antirheumatic drug. That combination results in inhibiting or treating SLE and/or pSS in the subject.

12 Claims, 12 Drawing Sheets

(4 of 12 Drawing Sheet(s) Filed in Color)

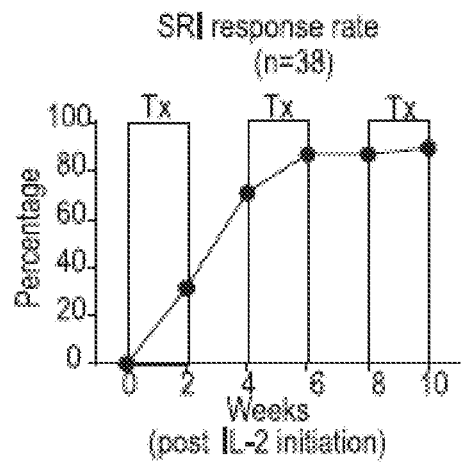
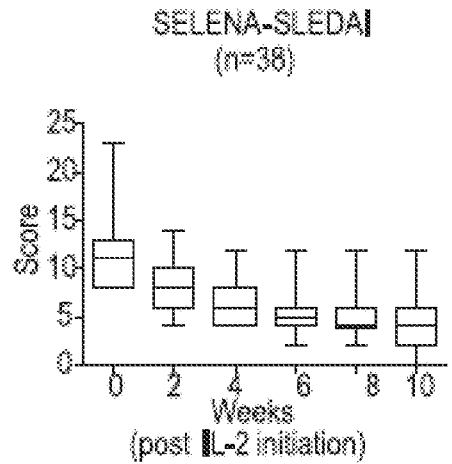
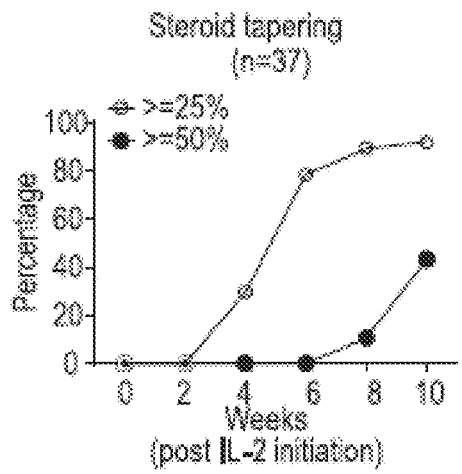
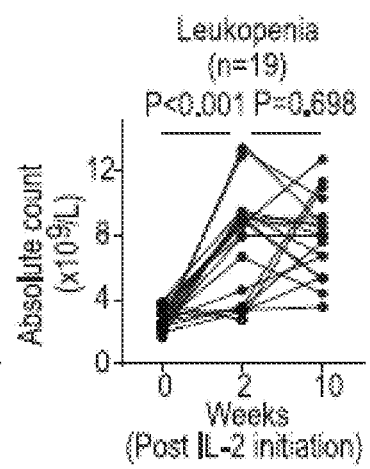
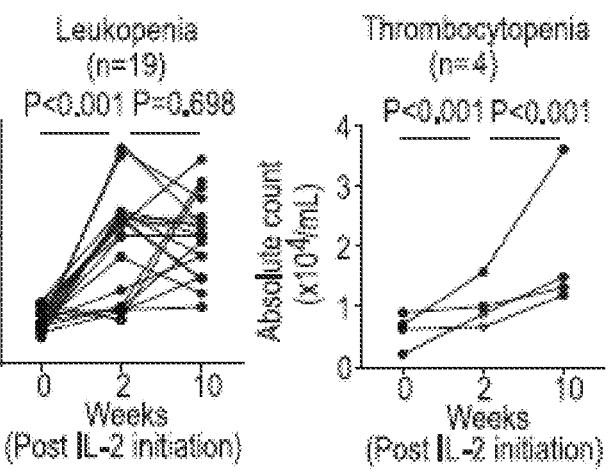
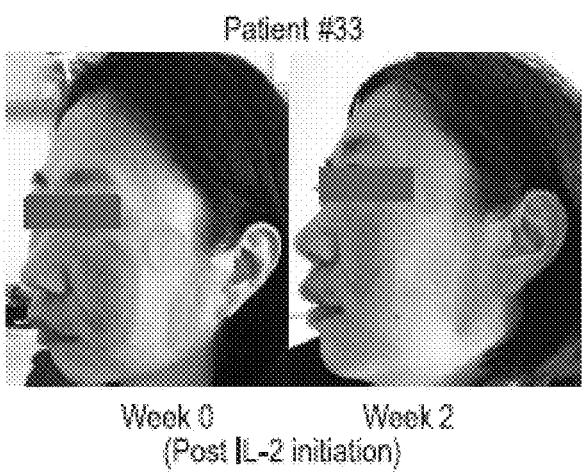
FIG. 1E

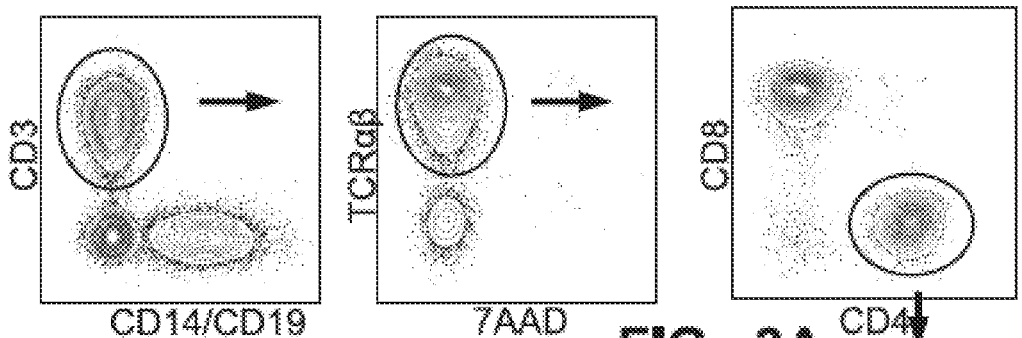
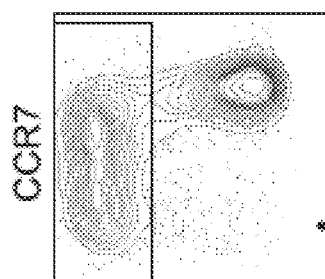
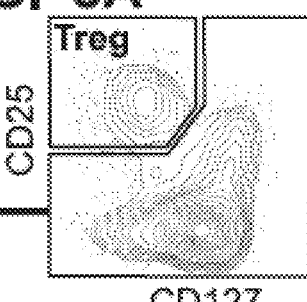
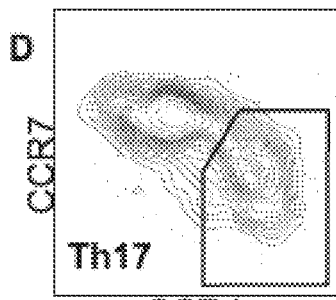
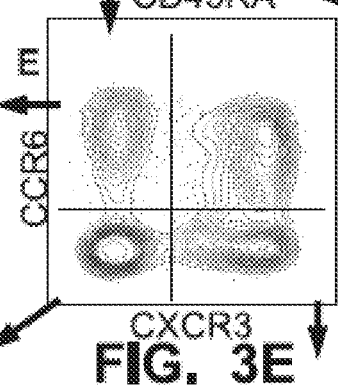
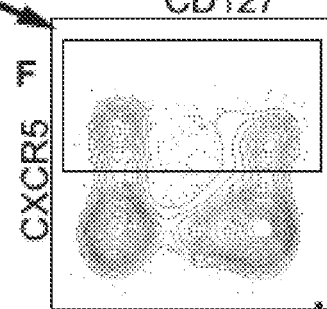
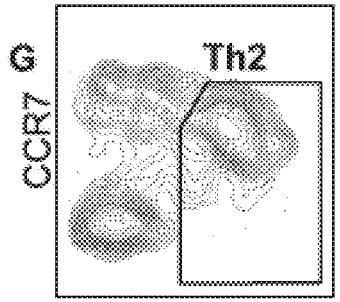
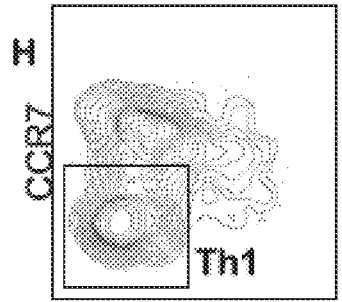
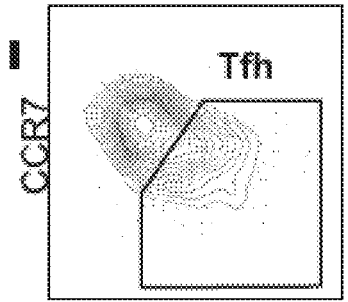
| | |
|---|---|
| Treg | CD25high CD127low CD4+ CD8− CD3+ TCRαβ+ CD14− CD19− 7AAD− |
| Th1 | CXCR3+ CCR6− CCR4− CCR7low CD4+ CD8− CD3+ TCRαβ+ CD14− CD19− 7AAD− |
| Th2 | CCR4+ CXCR3− CCR6− CCR7low CD4+ CD8− CD3+ TCRαβ+ CD14− CD19− 7AAD− |
| Th17 | CCR4+ CCR6+ CXCR3− CCR7low CD4+ CD8− CD3+ TCRαβ+ CD14− CD19− 7AAD− |
| Tfh | CXCR5+ PD-1+ CCR7low CD4+ CD8− CD3+ TCRαβ+ CD14− CD19− 7AAD− |

| Treg | Foxp3+ CD25+ CD4+ B220- |
| Th1 | IFN γ+ CD44high CD4+ B220- |
| Th17 | IL-17 + CD44high CD4+ B220- |
| Tfh | Bcl6+ CXCR5high Foxp3-CD4+ B220- |
| GC | Bcl6+ GL-7+ B220+ CD4- |

METHOD FOR PREDICTING AND MONITORING THE EFFICACY OF LOW-DOSE IL-2 AND HYDROXYCHLOROQUINE THERAPY IN AUTOIMMUNE DISEASES AND ITS LONG-TERM USE IN AUTOIMMUNE-RELATED CONDITIONS

PRIORITY CLAIM

This application claims priority to U.S. provisional patent application Ser. No. 62/807,856, filed on Feb. 20, 2019.

FIELD OF THE INVENTION

The present invention relates to a novel combination of IL-2 and hydrochloroquine based therapies to at least inhibit and effectively treat systemic lupus erythematosus (SLE) and/or primary Sjögren's syndrome (pSS).

BACKGROUND OF THE INVENTION

Interleukin-2

Interleukin-2 (IL-2) was molecularly cloned in 1983 and was originally called T cell growth factor because of its ability to stimulate T lymphocytes in vitro. It is a protein with a reported molecular weight of between approximately 13 kDa and 17 kDa and an isoelectric point of approximately 6 to 8.7.

Recombinant human IL-2 (rhIL-2) was used to treat patients with melanoma and other cancers from 1984. Due to its function in supporting T-cell proliferation, survival and effector differentiation, IL-2 treatment, when used in high dose, demonstrated efficacy in a fraction of patients. The approval of IL-2 therapy in certain types of solid tumors significantly contributed to the concept of cancer immunotherapy.

IL-2 has been shown to be critical for the development and maintenance of T cell subsets including regulatory T cells (Treg). Deficiencies of Treg cells have been found in various autoimmune diseases, including systemic lupus erythematosus (SLE), rheumatoid arthritis (RA), and Sjögren's Syndrome (SS).

For cancer immunotherapy, high dose of IL-2 is recommended and that high dose can be, for example, 60 or 72 million units/kg every 8 hours for 5 days, repeated every 6 to 12 weeks. The discoveries of regulatory T (Treg) cells that play a central role in maintaining immune tolerance and a key role of IL-2 for the development of Treg cells inspired an alternative application of IL-2 therapy. Instead of promoting immunity by high-dose IL-2, a series of recent clinical trials evaluated the application of low-dose IL-2 in inflammatory and autoimmune disorders such as hepatitis-C-associated vasculitis, graft-versus-host disease, type 1 diabetes, alopecia, and systemic lupus erythematosus (SLE). The benefit of low-dose IL-2 therapy is considered to be based on the expansion of immune tolerance-inducing Treg cells and also contributed by the suppression of follicular helper T (TFH) cells that induce autoantibody production and IL-17-producing helper T (TH17) cells that participate in tissue inflammation.

Admittedly, the above-identified paragraph seems to convey that low-dose IL-2, by itself, is a known treatment for SLE. That implication is erroneous for the following reasons:

(1) In one of IL-2's registered indications, adjunct treatment of renal cell carcinoma (RCC), the results were that less than 10% of the patients responded to the IL-2 treatment. This limited efficacy of IL-2 is now partly explained by the accepted knowledge that IL-2 also plays a major role in the peripheral survival and suppressive function of regulatory T (Tregs) cells, which are known to suppress anti-tumor effector responses.

(2) IL-2/IL-2 receptor (IL-2R) signalling is important during immune responses of both effector T cells (Teff) and Treg. On the one hand, extensive IL-2R signalling is necessary for the development of terminally differential short-lived Teff cells that exhibit enhanced functional activity, and for eliciting proper T cell memory. On the other hand, IL-2/IL-2R signalling is essential for Treg development and homeostasis as confirmed by the fact that IL-2 knock-out mice lack Tregs. Noteworthy, IL-2 or IL-2R deficient mice are able to mount effector immune responses, as notably attested by their development of severe T-cell mediated auto-immune diseases (AID).

(3) These different consequences of IL-2 signalling abnormalities are now explained by the fact that both quantitative and qualitative differences in IL-2/IL-2R signalling regulate Treg and Teff. Tregs appear to require low IL-2/IL-2R signalling threshold to support their development and peripheral homeostasis. IL-2 administration has been shown to lead to marked expansion and activation of Tregs in mice and humans.

(4) Nowadays, IL-2 continues to be utilized primarily for cancer immunotherapy and has not been fully investigated in association with human auto-immune diseases or, more generally, in human diseases caused by an undesirable immune response. This lack of investigation is because of the perceived and expected risks associated with such treatment. Indeed, the capacity of IL-2 to stimulate Teffs carries the risk of activating the very effector T cells that mediate the disease and therefore to aggravate the disease.

When Low Dose IL-2 was Previously Investigated

Administering low IL-2 doses—for example and not limited to 0.1 MIU/day to 3.5 MIU/day—have been disclosed in (a) U.S. Pat. No. 9,669,071 to Klatzmann and (b) U.S. Pat. No. 10,183,061 to Dorothée to treat, prevent or cure specific autoimmune diseases.

Klaztman discloses its low dose IL-2 treatment is effective on type I diabetes (see, Klatzmann's claim 1), type I diabetes (see, Klatzmann's claim 11), and baldly suggests in the abstract, "and other autoimmune and/or inflammatory diseases" based upon the assertion that "The inventors have proceeded further with testing low-dose IL-2 in another autoimmune disease, namely type I diabetes, thereby confirming the interest of low-dose IL-2 in treating autoimmune, immune-related or inflammatory disorders" (see, Klatzmann, column 6, lines 16-20) without providing any data to substantiate the assertion that low-dose IL-2 is effective in treating all autoimmune, immune-related or inflammatory disorders.

In contrast, Dorothée discloses its low dose IL-2 treatment addresses early onset of Alzheimer's disorder (see, Dorothée's claim 1) and related disorders such as "cognitive deficits" (see, claim 20) and mild cognitive impairment (see, Dorothée's claim 36) in order to improve cognitive function and reduce non-cognitive neurobehavioral deficits (see, respectively Dorothée's claims 16 & 54; and 35, 17, & 55).

Both Klatzmann and Dorothée documents also generically disclose bald assertions that low-dose IL-2 treats a number of inflammatory, immune-related or autoimmune diseases, without sufficient data to support those assertions.

The disclosures of Klatzmann and Dorothée regarding low-dose IL-2 are directed to very specific diseases. That may be a result of Zein's broad disclosure in WO2002078624. Zein disclosed, "IL-2 has been used for the treatment of cancer and infectious diseases but has substantial systemic toxicity and a narrow therapeutic index . . . . And although parenteral high-dose IL-2 (e.g. $>3 \times 10^6$ IU/day) has been shown to have beneficial effects in patients with cancer, common variable immunodeficiency (CVID), and human immunodeficiency virus (HIV), use and acceptance has been limited by this toxicity, especially capillary leak and flu-like symptoms. In view of IL-2 toxicity when given by the parental or subcutaneous routes, newer means for the therapeutic delivery of IL-2 are clearly needed." See, Zein's page 1, lines 4-14. At page 8, lines 2-19; Zein further reported, "Aerosolized IL-2 liposome formulations may be administered as a therapeutic agent to treat patients with immune deficiency or chronic viral infections, including hepatotrophic viral infections and hepatitis. Administration of aerosol 11-2 liposomes formulations includes administration by a health care provider and self-administration by the patient. Administration may be accomplished using a nebulizer. Aerosol treatments may take place repeatedly on any given day, for example, 1, 2, 3, 4 or 5 times per day. Aerosol treatments may take place every day or at less frequent intervals, for example, every other day or weekly. Aerosol treatments may continue for a short period of time, for example, for a time period of 1 to 5 weeks. Treatments may also continue long term, for example for a time period of 1 to 11 months, for 1 to 5 years or longer. Any dosage of IL-2 may be administered. Dosages to be administered include, but are not limited to, 0.1, 0.5, 1.0, 2, 2.5, 5.0 and $10\times10^6$ IU/day. IL-2 liposome formulations may be administered using dose escalation and/or induction therapy. Dose escalation refers to an incremental increase in the dose of 11-2 liposome formulation or its frequency of administration."

That means, Zein reported a genus disclosure that low dose IL-2 could address an autoimmune disease; in contrast Klaztmann and Dorothée reported essentially a species disclosure that low dose IL-2 can treat specific autoimmune diseases—respectively, Alzheimer's and diabetes. Klatzmann and Dorothée disclose low dose IL-2 induces Tregs without inducing Teff. The increased inducement of Tregs, according to those references, reduces the inflammation in many inflammatory diseases. As illustrated in this application, that bald assertion is misleading in relation to the diseases addressed in this application.

Hydroxychloroquine

Hydroxychloroquine is an immunomodulatory drug that was initially developed for treatment of malaria. It is now approved by the US Food and Drug Administration for treatment of discoid lupus, systemic lupus erythematosus, and rheumatoid arthritis. It is also approved to treat malaria; however, of the several malarial parasites, only *Plasmodium falciparum* can still be cured by hydroxychloroquine, and growing resistance limits the geographic locations where this drug can be used effectively. Antimalarial drugs were discovered shortly before World War II. Hydroxychloroquine production was industrialized during the war because malaria was a leading cause of disease among soldiers, especially those deployed to the South Pacific.

A serendipitous consequence of the mass use of antimalarials during World War II was the discovery that hydroxychloroquine could be used to treat inflammatory arthritis and lupus. Eight years after the war ended, Shee (in an article entitled "Lupus erythematosus treated with chloroquine", Lancet 1953; 265(6778):201-202. pmid: 13070595) reported that chloroquine had a beneficial effect on lupus and rheumatoid arthritis in US soldiers. Hydroxychloroquine is now the most commonly prescribed antimalarial for treatment of autoimmune disease.

A primary mechanism by which hydroxychloroquine modulates systemic lupus erythematosus is by suppressing activation of Toll-like receptors (that are a class of proteins that play a key role in the innate immune system; and are single, membrane-spanning, non-catalytic receptors usually expressed on sentinel cells such as macrophages and dendritic cells, that recognize structurally conserved molecules derived from microbes), which exist on the surface of endosomes and play a significant role in the innate immune response and in autoimmune disease(s). Toll-like receptor activation is necessary for the expression of interferon-regulated genes and production of tumor necrosis factor alpha, which are key in the cell-mediated inflammatory response. Hydroxychloroquine inhibits Toll-like receptor activation by binding directly to nucleic acids in the activation pathway. In vitro studies show that blocking the activation pathway blunts the body's primary cell-mediated inflammatory response; in vivo studies show that use of hydroxychloroquine is strongly correlated with a reduction in interferon alpha levels. The powerful effect of hydroxychloroquine on the cell-mediated pattern of inflammation found in lupus is consistent with this theory.

Hydroxychloroquine has consistently demonstrated significant and multifaceted benefit in patients with systemic lupus erythematosus. A systematic review of many articles concluded that hydroxychloroquine decreases lupus flares and decreases mortality rates in lupus patients by at least 50%, with a high level of evidence. Beneficial effects that had a moderate level of evidence were an increase in bone mineral density, fewer thrombotic events, and fewer cases of irreversible organ damage. The preventive effect of hydroxychloroquine on thrombosis in lupus patients has been consistently demonstrated and is a key reason hydroxychloroquine is considered a cornerstone of therapy in this disease. A nested case-control study of patients with lupus and thromboembolism demonstrated an odds ratio (a measure of association between an exposure and an outcome) of 0.31 and relative risk reduction of 68% for those using anti-malarials.

Despite widespread use, hydroxychloroquine has not demonstrated positive clinical effects when used to treat primary Sjögren syndrome. Most notably, a 2014 randomized controlled trial of hydroxychloroquine vs placebo in 120 Sjögren patients found no significant improvement in primary symptoms of dryness, pain, or fatigue after 6 months of therapy. See, Gottenberg J E, Ravaud P, Puechal X, et al. Effects of hydroxychloroquine on symptomatic improvement in primary Sjogren syndrome. JAMA 2014; 312(3):249-258. doi:10.1001/jama.2014.7682

Patent that Disclosed IL-2 and Lupus Treatment

In U.S. Pat. No. 10,174,121; Benatuil et al. disclosed "an anti-CD40 antibody, or antigen-binding portion thereof . . . e.g. Ab102, is used in combination with a disease-modifying antirheumatic drugs (DMARD) to treat SLE. An example of a DMARD includes, but is not limited to, hydroxychloroquine (Plaquenil), chloroquine, methotrexate (Rheumatrex), leflunomide (Arava), sulfasalazine, or combinations thereof." Bracketed material added for clarity.

Later in the patent, Benatuil suggests combining the anti-CD40 antibody with "cytokine suppressive anti-inflammatory drug(s) (CSAIDs); antibodies to or antagonists of other human cytokines or growth factors, for example, IL-1, IL-2, IL-3, IL-4, IL-5, IL-6, IL-7, IL-8, IL-15, IL-16, IL-18, IL-21, IL-31, interferons, EMAP-II, GM-CSF, FGF, EGF, PDGF, and endothelin-1, as well as the receptors of these cytokines and growth factors."

Nowhere does Benatuil teach or suggest a combination of IL-2, of any dose, with a disease-modifying antirheumatic drugs (DMARD) as an effective treatment of SLE and/or Sjögren's syndrome.

SUMMARY OF THE INVENTION

A method of inhibiting or treating systemic lupus erythematosus (SLE) and/or primary Sjögren's syndrome (pSS) in a subject in need thereof is disclosed. The method calls for administering to the subject a therapeutically effective low-dose amount of interleukin-2 in combination with a therapeutically effective amount of a disease-modifying antirheumatic drug, like hydroxychloroquine. That combination of interleukin-2 and the disease-modifying antirheumatic drug results in inhibiting or treating SLE and/or pSS in the subject.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A to 1E illustrates clinical responses to the claimed method in SLE in relation to: (FIG. 1A) Systemic Lupus Erythematosus Responder Index (SRI) response rate, (FIG. 1B) Systemic Lupus Erythematosus Disease Activity Index (SELENA-SLEDAI), (FIG. 1C) steroid tapering, (FIG. 1D) Leukopenia and Thrombocytopenia; and (FIG. 1E) comparison photographs of patients 33 and 8 at week zero and week 2 of the claimed method;

FIGS. 2A to 2E illustrate immunological responses to the claimed method in SLE in relation to: (FIG. 2A) Treg cells, (FIG. 2B) Tfh cells, (FIG. 2C) Th17 cells, (FIG. 2D) Th1 cells, and (FIG. 2E) Th2 cells;

FIGS. 3A to 3I illustrates the phenotypic characterization of T-cell subpopulations by flow cytometry for the claimed method and the gating strategy for the following sets: FIGS. 3A and 3C show the Treg cells were defined as CD3+ CD4+ CD25high CD127low, FIGS. 3B, 3D, and 3F illustrate the Tfh cells were defined as CD3+ CD4+ CXCR5+ PD1high CCR7 low 6, FIGS. 3D, 3E, and 3F illustrate Th1 cells were defined as CD3+ CD4+ CXCR3+ CCR6− CCR4− CCR7 low; FIGS. 3D, 3G, and 3H convey that Th2 cells were defined as CD3+ CD4+ CXCR3+ CCR6− CCR4+ CCR7 low and FIGS. 3E, 3D, 3E, 3F, 3G, 3H and 3I illustrate Th17 cells were defined as CD3+ CD4+ CXCR3− CCR6+ CCR4+ CCR7 low 26;

FIGS. 4A to 4D illustrate clinical responses to the claimed method in relation to: (FIG. 4A) Complement C3, (FIG. 4B) Complement C4, (FIG. 4C) Anti-double stranded DNA antibody (Anti-dsDNA) Immunoglobulin G (IgG), and (FIG. 4D) Urine protein;

FIGS. 5A to 5I illustrate clinical responses of the claimed method to the placebo method, wherein both subject sets were administered hydroxychloroquine, in relation to: (FIG. 5A) time against change in European League Against Rheumatism (EULAR) Sjögren's Syndrome Patient Reported Index (ESSPRI) score, (FIG. 5B) time against change in EULAR Sjögren's syndrome disease activity index (ESSDAI) score, (FIG. 5C) time against change in multidimensional fatigue inventory (MFI-20) score, (FIG. 5D) time against change in diffusing capacity of the lungs for carbon monoxide percentage (DLCO %), (FIG. 5E) time against change in forced vital capacity percentage (FVC %)—measurement shows the amount of air a person can forcefully and quickly exhale after taking a deep breath —, (FIG. 5F) time against change in beta-2-microglobulin (B2MG) (ug/L), (FIG. 5G) time against N-acetyl-β-D-glucosaminidase. (NAG) (U/L), (FIG. 5H) time against change in retinol-binding proteins (RBP) (mg/L), and (FIG. 5I) time against platelet (PLT) recovery rate (%);

FIGS. 6A to 6F illustrate immunological parameters after low-dose IL-2 therapy in Sjögren's syndrome in relation to: (FIG. 6A) time against change in CD25$^{hi}$ CD127$^{lo}$ in CD4$^{+}$ T cells (%); (FIG. 6B) time against change in CD25$^{hi}$ CD127$^{+}$ in CD19$^{+}$ B cells (%); (FIG. 6C) time against change in IL-10 expression in CD19+ T cells (%); (FIG. 6D) time against change in IL-2 (pictogram (pg)/milliliter (ml)); (FIG. 6E) time against change in IL-17A (pg/ml) and (FIG. 6F) time against change in IFN-α (pg/ml);

FIG. 7A to 7D illustrate phenotypic characterization of Treg and Breg after low-dose IL-2 therapy in relation to: (FIG. 7A) CD127 against change in CD25 at Pre-IL-2 application and Post-IL-2 application; (FIG. 7B) CD127 against change in CD25 at Pre-placebo application and Post-placebo application; (FIG. 7C) CD24 against change in CD27 at Pre-IL-2 application and Post-IL-2 application; (FIG. 7D) CD24 against change in CD27 at Pre-placebo application and Post-placebo application;

FIGS. 10A to 10B illustrates the immunological effects of different doses of IL-2 in mouse immunized with OVA in CFA wherein FIG. 10A illustrates the method on a timeline, while FIG. 10B illustrates the immunological effects of different doses of Tref, Th1, Th17, Tfh, and GC.

FIGS. 11A to 11E illustrates the immunological response and comparison between PBS and different doses of IL-2 in a mouse; wherein FIG. 11A represents Treg cells—cell number per $10^6$ splenocytes compared to: (a) PBS, (b) 10,000 IL-2 IU; (c) 30,000 IL-2 IU and (d) 100,000 IL-2 IU; FIG. 11B represents Th1 cells—cell number per $10^6$ splenocytes compared to: (a) PBS, (b) 10,000 IL-2 IU; (c) 30,000 IL-2 IU and (d) 100,000 IL-2 IU; FIG. 11C represents Th17 cells—cell number per $10^6$ splenocytes compared to: (a) PBS, (b) 10,000 IL-2 IU; (c) 30,000 IL-2 IU and (d) 100,000 IL-2 IU; FIG. 11D represents T fh cells—cell number per $10^6$ splenocytes compared to: (a) PBS, (b) 10,000 IL-2 IU; (c) 30,000 IL-2 IU and (d) 100,000 IL-2 IU; and FIG. 11E represents GC B cells—cell number per $10^6$ splenocytes compared to (a) PBS, (b) 10,000 IL-2 IU; (c) 30,000 IL-2 IU and (d) 100,000 IL-2 IU.

DETAILED DESCRIPTION OF THE INVENTION

Figure 2A:
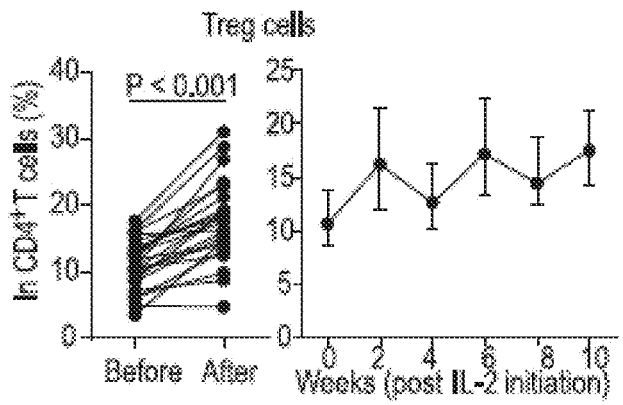

An object of the invention relates to a composition and a method to restore the imbalance of the immune system in a human subject. The composition and method comprises administering low-dose of IL-2—for example and not limited to 0.1 Million International Units (MIU) per day or every other day; to 3.5 MIU/day or every other day; or variations there of as dependent on the patient's condition and reaction to the claimed method —, to stimulate regulatory T lymphocytes (Tregs) without, preferably substantially, inducing effector T lymphocytes (Teffs) in combination with a therapeutically effective amount of disease-modifying antirheumatic drugs (DMARD)—for example, hydroxychloroquine (HCZ) 200 mg to 400 mg Bid.

First of all, in the experiments HCZ was provided to ensure basic treatment, followed by a comparison of (a) before IL-2 treatment and (b) after IL-2 treatment at two weeks, four weeks, six weeks, eight weeks and ten weeks to treat SLE and/or pSS. This combination resulted in unexpected and superior results in treating and/or inhibiting SLE and/or pSS.

The low-dose IL-2 with the therapeutically effective amount of disease-modifying antirheumatic drugs (DMARD) to treat SLE and/or pSS also addresses the following additional objectives:
(A) acting by specific Treg expansion/activation, including the markers of specific Tissue resident Treg cells, such as Treg expression of CCR2, CCR4, CCR5, CCR7, CTLA-4, ICOS and P-/E-selectin ligands;
(B) acting by specific Breg expansion/activation to rebalance the B cell homostasis (see, for example, FIGS. 7A-D, 8A-B and 9A-B); and
(C) acting by specific NK cell expansion/activation, such as $CD56^{bright}$ NK cells.

A low dose of 1 million IU of IL-2, SC, every other day and HCZ 200 mg Bid, PO, every day regimen was well tolerated in a double-blinded trial that studied the effect on SLE and/or pSS.

Example 1: Low-Dose IL-2 and Hydroxychloroquine in SLE

An open-label study regarding the safety and clinical impact of low-dose recombinant human IL-2 (rhIL-2) in active SLE was performed. This study showed for the first time that low-dose IL-2 selectively expansion of Treg cell numbers and reduction in Tfh and Th17 effector CD4+ T cell subsets in humans.

The study recruited male and female patients aged 18-65 years with SLE, diagnosed according to the 1997 revised classification criteria of the American College of Rheumatology, with moderate-to-severe disease activity (Safety of Estrogens in Lupus Erythematosus National Assessment version of the Systemic Lupus Erythematosus Disease Activity Index (SELENA-SLEDAI)>8). All patients had active disease at the time of enrolment despite at least 4 weeks of stable background treatment with corticosteroids (≤1.0 mg/kg prednisone or equivalent) and/or with antimalarials, nonsteroidal anti-inflammatory drugs or immunesuppressants. See, Table 1.

TABLE 1

Baseline characteristics of SLE patients (n = 40)

| Characteristic | Value |
| --- | --- |
| Age, year, median (range) | 31 (18-60) |
| Female/Male | 37/3 |
| Weight, kg, median (range) | 54 (42-80) |
| Height, cm, median (range) | 160 (150-175) |
| Area, $m^2$, median (range) | 1.61 (1.36-1.92) |
| Duration of SLE, year, median (range) | 5 (0.5-20.0) |
| Prednisone dose, mg/day, median (range) | 30 (0-60) |
| Use of concomitant agents (no. of patients) | |
| Hydroxychloroquine | 37 |

Exclusion criteria included: active severe neuropsychiatric manifestations of SLE; a history of treatment with rituximab or other biologics; use of high-dose corticosteroids (≥1.0 mg/kg) in the preceding month; severe co-morbidities including heart failure (≥grade III as defined by the New York Heart Association's functional classification system (NYHA)), renal insufficiency (creatinine clearance ≤30 ml/min), or hepatic insufficiency (alanine aminotransferase or aspartate aminotransferase ≥2 times of the upper limit of the normal range); active infection (hepatitis B or C virus, Epstein-Barr virus, human immunodeficiency virus or *Mycobacterium tuberculosis*) or history of chronic infection; malignancy; pregnancy or lactation in females.

FIGS. 1A-1E, 2A-2E, and 3 convey information regarding the open-label study evaluated the efficacy of low-dose rhIL-2 (recombinant human IL-2Ser125, Beijing SL Pharma) in patients with active SLE. The rhIL-2, produced in *E coli*, is approved by the State Food and Drug Administration, China, and has comparable bioactivity to PROLEUKIN® brand of an injectable, recombinant form of interleukin-2 drug (the Proleukin trademark is currently owned by Novartis Vaccines & Diagnostics, Inc.). Three cycles of rhIL-2 were administered subcutaneously at a dose of 1 million IU every other day for 2 weeks (a total of 7 doses), followed by a 2-week break. After the initiation of IL-2 therapy, no increase in any other treatments for SLE was permitted. Clinical and laboratory data were measured at baseline and every 2 weeks thereafter until week 12. During the study, corticosteroid doses were tapered at the discretion of the treating physician according to European League Against Rheumatism (EULAR) evidence-based recommendations on the management of corticosteroid therapy. See for example and not limited to; Hoes et al., EULAR evidence-based recommendations on the management of systemic glucocorticoid therapy in rheumatic diseases; Ann Rheum Dis; 2007 December; 66(12): 1560-7. Epub 2007 Jul. 27; and Duru et al., EULAR evidence-based and consensus-based recommendations on the management of medium to high-dose glucocorticoid therapy in rheumatic diseases; Ann Rheum Dis; 2013 December; 72(12):1905-13. doi: 10.1136/annrheumdis-2013-203249. Epub 2013 Jul. 19. Briefly, patients' disease activity was evaluated every 2 weeks, and patients were advised to taper 5-10%° of the current dose of corticosteroids if disease activity was reduced. HCZ was not changed during the study and the dosage ranged from 200 mg to 400 mg per day.

Protocol-specific immunophenotypic analysis of peripheral blood lymphocyte subsets was performed at baseline and every 2 weeks thereafter until week 12 (week 0, 2, 4, 6, 8, 10 and 12). Peripheral blood mononuclear cells (PBMCs) were incubated with fluorophore-conjugated monoclonal antibodies listed at table 2.

TABLE 2

Antibodies Used in Flow Cytometric Analysis.

| Antigen | Clone | Fluorochrome | Vendor |
| --- | --- | --- | --- |
| CD14 | M5E2 | Brilliant Violet 785 | Biolegend |
| CD19 | HIB19 | Brilliant Violet 785 | Biolegend |
| CD3 | OKT3 | Brilliant Violet 650 | Biolegend |
| TCRαβ | IP26 | FITC | Biolegend |
| CD4 | RPA-T4 | Alexa Fluor 700 | Biolegend |
| CD8 | RPA-T8 | Brilliant Violet 510 | Biolegend |
| CD25 | M-A251 | PE-CF594 | BD Biosciences |
| CD127 | A019D5 | Brilliant Violet 605 | Biolegend |
| CD45RA | HI100 | APC-Cy7 | Biolegend |
| CCR7 | G043H7 | PE-Cy7 | Biolegend |
| CXCR3 | G025H7 | Brilliant Violet 421 | Biolegend |
| CCR6 | G034E3 | PE | Biolegend |
| CXCR5 | RF8B2 | Alexa Fluor 647 | BD Biosciences |
| CCR4 | TG6 | PerCP-Cy5.5 | Biolegend |
| PD-1 | EH12.2H7 | Brilliant Violet 711 | Biolegend |

Relative proportions of Treg, Tfh, Th1, Th2 and Th17 cell subsets were analyzed by flow cytometry using a BD FACSAria® III brand sorter and FlowJo® brand software (both FACSAria® III sorter and FlowJo® software are currently provided by BD which currently has an office at 1 Becton Drive, Franklin Lakes, N.J. 07417) as follows:

Treg cells were defined as CD3+ CD4+ CD25high CD127low,

Tfh cells were defined as CD3+ CD4+ CXCR5+ PD1high CCR7 low 6,

Th1 cells were defined as CD3+ CD4+ CXCR3+ CCR6− CCR4− CCR7 low,

Th2 cells were defined as CD3+ CD4+ CXCR3+ CCR6− CCR4+ CCR7 low and

Th17 cells were defined as CD3+ CD4+ CXCR3− CCR6+ CCR4+ CCR7 low 26.

The detailed gating strategy for these subsets is outlined at FIGS. 3A to 3I.

Statistical Analyses

All statistical analyses were carried out using GraphPad Prismt brand analysis and graphing solution purpose software (Version 5.0, provided by GraphPad Software which currently has an office located at 2365 Northside Dr.; Suite 560; San Diego, Calif. 92108) or SPSS® brand analysis and graphing solution purpose software (version 17.0, provided by IBM which currently has an office at New Orchard Road, Armonk, N.Y. 10504). A per-protocol analysis was undertaken, excluding patients who did not complete treatment. Wilcoxon matched-pairs signed rank test was used for paired comparison of differences in clinical characteristics and laboratory parameters between baseline and indicated time points.

As expressed at https://influentialpoints.com/Training/wilcoxon_matched_-pairs_signed_rank_test-principles-properties-assumptions.htm, "The Wilcoxon signed-ranks test is a non-parametric equivalent of the paired t-test. It is most commonly used to test for a difference in the mean (or median) of paired observations—whether measurements on pairs of units or before and after measurements on the same unit. It can also be used as a one-sample test to test whether a particular sample came from a population with a specified median. Unlike the t-test, the paired differences do not need to follow a normal distribution. But . . . to test the median (=mean) difference, the distribution each side of the median—must have a similar shape. In other words, the distribution of the differences must be symmetrical. If the distribution of the differences is not symmetrical, you can only test the null hypothesis that the Hodges-Lehmann estimate of the median difference is zero. Unlike most rank tests, this test outcome is affected by a transformation before ranking since differences are ranked in order of their absolute size. It may thus be worth plotting the distribution of the differences after an appropriate transformation (for example logarithmic) to see if it makes the distribution appear more symmetrical. A signed-ranks upon paired samples is less powerful than the t-test (relative efficiency is about 95%) providing the differences are normally distributed. If they are not, and cannot be transformed such that they are, a paired t-test is not appropriate and the non-parametric test should be used."

The paired-sample t-test was used to compare immunological features between baseline and each indicated time point during the IL-2 therapy, as well as PBS group and different doses of IL-2 group in immunized mice. Repeated-measures analysis of variance was used to calculate within-group P values.

Patients

Forty patients were enrolled, with a median age of 31 years (range, 18 to 60) and disease duration of 5 years (range, 0.5 to 20). The female to male ratio was 12:1. Characteristics of the patients are shown at Table 1. The median baseline daily dose of prednisone was 30 mg (range, 0 to 60); other concomitant treatments are shown at Table 1. Two of the enrolled patients withdrew from the study at week 8: one was changed to belimumab treatment due to personal preference, the other was changed to cyclophosphamide treatment due to the patient's wish to reduce the frequency of hospital visits.

Safety of Low-Dose IL-2 and Hydrochloroquine

Thirty-eight patients completed all three cycles of IL-2 treatment. No serious adverse events occurred. See, Table 3, and FIGS. 10A-B and 11A-E.

TABLE 3

Adverse Events of Patients during rhIL-2 Therapy (n = 40).

| Adverse events | No. of Patients |
| --- | --- |
| Injection-site reaction | 5 |
| Fatigue | 1 |
| Fever | 1 |
| Infection | 0 |

Injection site reactions were observed in 5 patients (13.2%). Influenza-like symptoms (fatigue or fever) occurred in 2 patients (5.3%). All adverse events were resolved without any intervention. Notably, no infection was observed during the 12-week period of the IL-2 treatment. The two patients who withdrew prior to completing 12 weeks of observation did not withdraw as a result of any adverse event. No obvious side effects were seen during the HCZ protocol.

Clinical Efficacy of Low-Dose IL-2 and Hydrochloroquine in SLE

All 38 patients who completed therapy had lower disease activity at the end of the study compared to baseline. The proportion of patients who achieved a Systemic Lupus Erythematosus Responded Index (SRI) response was 31.6% at week 2 and 71.1% at week 4. As expressed in the abstract by Luijten et al. in an article entitled, "The Systemic Lupus Erythematosus Responder Index (SRI); a new SLE disease activity assessment that can be obtained" at Automimmun Rev.; 2012 March; 11(5):326-9. doi: 10.1016/j.autrev.2011.06.011. Epub 2011 Sep. 18; "Systemic Lupus Erythematosus (SLE), because of its complex and multisystemic presentation, lacks a reliable and sensitive gold standard for measuring disease activity. In addition, there is no standardized method for defining response to therapy. Several disease activity indices have been developed over the years, each with their own positive and negative aspects. Growing insight in the pathogenesis of inflammatory diseases like SLE leads to the introduction of specific targeted biologic therapies. To investigate the efficacy of these new biologic agents, disease activity must be monitored regularly by a reliable and validated instrument. Recent studies on new biologics for treatment of SLE use a new composite measurement for disease activity and response in SLE. This new disease activity assessment, called SLE Responder Index (SRI), comprises criteria from three different internationally validated indices, [Safety of Estrogens in Lupus Erythematosus National Assessment]-SLE Disease Activity Index (SELENA-SLEDAI), Physician Global Assessment (PGA) and the British Isles Lupus Assessment Group (BI-LAG) 2004." (Bracketed language added for definitional purposes.) The overall response rate was 89.5% (34/38 patients) at the end of 12 weeks of observation (see, FIG. 1A). The median SELENA-SLEDAI rapidly reduced after commencement of therapy (see, FIG. 1B) and the difference between median (median, range) SELENA-SLEDAI at baseline (11, 8-23) and week 12 (4, 0-12) was highly significant (see, Table 4).

TABLE 4

Clinical characteristics of patients before and after low-dose IL-2 therapy (n = 38).

| Characteristics | Baseline | week 12 | P value |
|---|---|---|---|
| SELENA-SLEDAI, median (range) | 11 (8-23) | 4 (0-12) | <0.001 |
| Rash, n (%) | 24 (63.2) | 4 (10.5) | <0.001 |
| Oral ulcers, n (%) | 3 (7.9) | 0 (0) | 0.079 |
| Serositis, n (%) | 5 (13.2) | 0 (0) | 0.021 |
| Raynaud's, n (%) | 6 (15.8) | 5 13.2) | 0.794 |
| Alopecia, n (%) | 14 (36.8) | 1 (2.6) | 0.034 |
| Arthritis, n (%) | 11 (28.9) | 1 (2.6) | 0.013 |
| Leukopenia, n (%) | 19 (50.0) | 1 (2.6) | <0.001 |
| Thrombocytopenia, n (%) | 4 (10.5) | 0 (0) | <0.001 |
| IgA, g/L, median (range) | 2.6 (0.81-6.5) | 2.76 (1.1-6.0) | 0.016 |
| IgG, g/L, median (range) | 14.2 (5.4-35.9) | 11.3 (3.6-22.5) | <0.001 |
| IgM, g/L, median (range) | 0.94 (0.12-2.42) | 0.967 (0.152-1.52) | 0.217 |
| C3, g/L, median (range) | 0.42 (0.118-1.46) | 0.809 (0.48-1.23) | <0.001 |
| C4, g/L, median (range) | 0.075 (0.017-0.54) | 0.158 (0.072-0.38) | <0.001 |
| Anti-dsDNA, IU/mL, median (range) | 417.9 (10-3987.5) | 175.9 (3.8-2413.2) | <0.001 |
| UrinePRO, g/24 h, median (range), n = 18 | 2.71 (0.68-21.78) | 0.83 (0.0-5.8) | 0.005 |
| Platelet, ×10$^{12}$/L, median (range) | 161 (62-337) | 218 (119-301) | <0.001 |
| WBC, ×10$^9$/L, median (range) | 3.95 (1.65-11.74) | 8.1 (2.56-10.47) | <0.001 |
| Lymphocyte, ×10$^9$/L, median (range) | 0.81 (0.17-2.22) | 1.60 (0.54-2.89} | <0.001 |
| Monocyte, ×10$^9$/L, median (range) | 0.31 (0.09-0.81) | 0.49 (0.29-0.91) | 0.034 |
| Neutrophil, ×10$^9$/L, median (range) | 2.34 (0.79-10.57) | 4.86 (0.12-8.52) | 0.001 |
| Eosinophil, ×10$^9$/L, median (range) | 0.02 (0-0.11) | 0.03 (0-0.17) | <0.001 |

Almost all lupus-related manifestations contributing to SELENA-SLEDAI score at baseline resolved during rhIL-2 treatment in majority of patients. Resolution of specific SLE manifestations was seen in the case of rash (20/24), alopecia (13/14), arthritis (10/11), fever (3/3) and serositis (5/5) were observed (P<0.05). Laboratory measures also demonstrated improvement (see, Table 4). Among the 18/38 patients with proteinuria at baseline, median 24-hour urine protein reduced from 2.71 g (range, 0.68 to 21.78) to 0.83 g (range, 0.0 to 5.8) (p=0.005) (see, Table 4). Both C3 and C4 increased significantly between baseline and week 12 (p<0.001), whereas anti-dsDNA titers decreased (P<0.001) (see, FIGS. 5A-I). Strikingly, 15 out of 19 patients with leukopenia and 2 of 4 patients with thrombocytopenia showed resolution of these manifestations at week 2, and the proportions of patients with resolution of leukopenia and thrombocytopenia at week 12 were 94.7% (18/19) and 100% (4/4), respectively (see, FIG. 1D). Examples of response to rhIL-2 are provided (see, FIG. 1E), wherein resolution of facial discoid and malar rashes was observed within 2 weeks. In contrast to these observations, Raynaud phenomenon—a condition where blood flow to your fingers, toes, ears, or nose is restricted or interrupted—, a feature of SLE not considered to represent immunological activity, did not improve in response to rhIL-2 administration.

Significant reductions in corticosteroid use were observed. All but one patient was on prednisone prior to rhIL-2 treatment. At week 12, 34/37 (91.9%) corticosteroid-treated patients had reduced prednisone dose compared to baseline by ≥25%, and 25 (67.6%) patients by ≥50%/(see. FIG. 1C). The median dose of prednisone was reduced from 30 mg/day (range, 0 to 60) at baseline to 17.5 mg/day (range, 0 to 30) at week 12 (p<0.001). The overall results illustrated a significant correlation with low dosage of IL-2 combined with a disease-modifying antirheumatic drugs (DMARD), preferably hydroxychloroquine, as an effective and unexpected treatment of SLE. See, Table 5 in combination with FIGS. 6A-F, 7A-D and 8A-B.

TABLE 5

Patient characteristics at baseline for pSS

| | Low-dose IL-2 (n = 30) With DMARD | Placebo (n = 30) With DMARD in 28 | p value |
|---|---|---|---|
| Age, years | 54 (45-60) | 48.5 (33-59) | 0.270 |
| Gender | | | |
| Female | 30 (100%) | 30 (100%) | NA |
| Male | 0 (0%) | 0 (0%) | NA |
| Weight, kg | 59.3 (9.1) | 59.2 (9.2) | 0.994 |
| Height, cm | 160.6 (5.8) | 160.3 (6.2) | 0.848 |
| BSA, m$^2$ | 1.58 (0.13) | 1.58 (0.14) | 0.952 |
| Duration of pSS at baseline, years | 5.0 (3.0-7.0) | 3.0 (1.50-8.50) | 0.311 |
| ESSPRI score | 5.0 (3.67-5.63) | 381.05 (153.95-987.58) | 0.239 |
| ESSDAI score | 3.0 (3.0-4.0) | 4.0 (3.0-5.0) | 0.773 |
| SF-36 score | 115.90 (104.90-123.65) | 110.0 (93.05-120.05) | 0.084 |
| MFI-20 score | 66.0 (59.25-77.50) | 72.0 (57.0-79.0) | 0.774 |
| WBC, ×10$^9$/L | 3.63 (3.27-4.93) | 4.66 (3.50-5.56) | 0.057 |
| HGB, g/L | 125.0 (120.75-130.0) | 123.0 (114.75-132.75) | 0.569 |
| Platelet, ×10$^9$/L | 200.0 (164.50-252.25) | 178.50 (142.50-214.75) | 0.308 |
| IgA, g/L | 3.98 (3.10-4.95) | 3.53 (2.62-5.05) | 0.586 |
| IgG, g/L | 22.60 (20.58-27.20) | 23.40 (22.03-25.55) | 0.392 |
| γ-G, % | 26.0 (23.25-30.85) | 25.60 (24.45-28.30) | 0.952 |

TABLE 5-continued

Patient characteristics at baseline for pSS

|  | Low-dose IL-2 (n = 30) With DMARD | Placebo (n = 30) With DMARD in 28 | p value |
|---|---|---|---|
| ESR, mm/hr | 31.50 (22.0-45.0) | 27.0 (13.75-45.75) | 0.359 |
| C3, g/L | 1.01 (0.89-1.14) | 0.97 (0.79-1.1) | 0.347 |
| C4, g/L | 0.192 (0.14-0.25) | 0.17 (0.15-0.21) | 0.295 |
| Anti-SSA, IU/mL | 202.6 (192.0-219.9) | 210.0 (197.2-216.7) | 0.346 |
| Anti-SSB, IU/mL | 62.9 (5.5-155.9) | 52.6 (7.5-195.4) | 0.440 |
| RF, IU/mL | 159.0 (29.35-398.5) | 97.10 (45.55-271.6) | 0.767 |
| RBP, mg/L | 0.25 (0.09-0.36) | 0.23 (0.12-0.50) | 0.652 |
| β2-MG, μg/L | 382.0 (79.3-868.8) | 381.1 (153.9-987.6) | 0.741 |
| NAG, U/L | 12.30 (7.73-18.18) | 12.15 (6.75-19.75) | 0.826 |
| FVC %, % | 103.45 (92.75-114.75) | 106.15 (100.0-110.13) | 0.599 |
| DLCO %, % | 103.45 (92.75-114.75) | 77.10 (70.35-87.43) | 0.483 |
| Current background medication |  |  |  |
| Hydroxychloroquine | 30 (100%) | 28 (93.3%) | 0.492 |

To assist in determining if background therapy contributed to the responses observed, an analysis of changes in disease activity was performed during rhIL-2 treatment in subsets of patients categorized according to background treatment (glucocorticoid+hydroxychloroquine, n=17; glucocorticoid+hydroxychloroquine+mycophenolate mofetil, n=13; glucocorticoid+hydroxychloroquine+cyclophosphamide, n=7). All these groups demonstrated reductions in SELENA-SLEDAI scores and anti-dsDNA IgG autoantibodies, as well as the increases of the levels of complement C3 and C4 (See, Table 6 and FIGS. 4A-D).

Complement is a system of 25 to 30 distinct cell membrane and plasma proteins, numbered C1 through C9. Once activated, the proteins interact with each other in a specific sequence called the complement cascade. The classical pathway is triggered by antigen-antibody complexes and includes participation of all complement proteins C1 through C9. The alternate pathway occurs when C3, C5, and C9 are activated without participation of C1, C2, and C4 or the presence of antigen-antibody complexes. Complement proteins act as enzymes that aid in the immunological and inflammatory response. The complement system is an important mechanism for the destruction and removal of foreign materials. Serum complement levels are used to detect autoimmune diseases. C3 and C4 are the most frequently assayed complement proteins, along with total complement.

Circulating C3 is synthesized in the liver and comprises 70% of the complement system, but cells in other tissues can also produce C3. C3 is an essential activating protein in the classic and alternate complement cascades. It is decreased in patients with immunological diseases, in whom it is consumed at an increased rate. C4 is produced primarily in the liver but can also be produced by monocytes, fibroblasts, and macrophages. C4 participates in the classic complement pathway.

TABLE 6

Comparison of efficacy at week 12 and week 24 for pSS

|  | Week 12 | | | | Week 24 |
|---|---|---|---|---|---|
|  |  |  |  | Difference |  |
|  | Low-dose IL-2 | Placebo | p value | (95% CI) | Low-dose IL-2 |
| ESSPRI score change from baseline | −0.81 (0.16) | 0.04 (0.17) | 0.001 | −0.85 (−1.32--0.38) | −0.95 (0.17) |
| ESSDAI score change from baseline | −0.99 (0.13) | −0.16 (0.13) | 0.000 | −0.82 (−1.19--0.45) | −0.109 (0.14) |
| SF-36 score change from baseline | 7.13 (3.15) | 2.15 (2.95) | 0.265 | 4.99 (−3.91-13.88) | 5.11 (4.02) |
| MFI-20 score change from baseline | −4.23 (1.12) | −0.94 (1.14) | 0.044 | −3.3 (−6.50--0.09) | −3.36 (1.18) |
| Fatigue, n (%) | 10 (45.5%) | 17 (81.0%) | 0.016 | 5.10 (1.29-20.17) | 11 (50.0%) |
| Arthritis, n (%) | 2 (25.0%) | 5 (71.4%) | 0.132 | 7.50 (0.76-74.16) | 3 (37.5%) |
| Parotid gland swelling, n (%) | 0 (0.0%) | 1 (50.0%) | 0.400 | NA | 0 (0.0%) |
| Purpura, n (%) | 0 (0.0%) | 1 (100.0%) | 0.333 | NA | 0 (0.0%) |
| Leukopenia, n (%) | 6 (54.5%) | 10 (100.0%) | 0.035 | 0.55 (0.32-0.94) | 8 (72.7%) |
| Thrombocytopenia, n (%) | 1 (20.0%) | 4 (57.1%) | 0.293 | 5.33 (0.38-75.78) | 2 (40.0%) |
| γ-G, % | 25.97 (3.85) | 26.49 (3.32) | 0.585 | −0.41 (−1.90-1.08) | 25.22 (3.67) |
| IgA, g/L | 3.91 (1.78) | 3.93 (1.64) | 0.980 | −0.01 (−0.41-0.40) | 3.71 (1.52) |
| IgG, g/L | 23.76 (5.44) | 22.80 (4.47) | 0.881 | 0.15 (−1.80-2.09) | 22.57 (4.94) |

TABLE 6-continued

Comparison of efficacy at week 12 and week 24 for pSS

| | | | | | |
|---|---|---|---|---|---|
| ESR, mm/hr | 25.36 (11.62) | 31.10 (21.4) | 0.054 | −6.93 (−14.00-0.14) | 28.04 (15.20) |
| C3, g/L | 0.97 (0.15) | 0.97 (0.25) | 0.176 | −0.04 (−0.1-0.02) | 0.99 (0.19) |
| C4, g/L | 0.20 (0.05) | 0.20 (0.06) | 0.319 | −0.01 (−0.03-0.01) | 0.21 (0.06) |
| RF, IU/mL | 215.87 (240.49) | 225.91 (309.40) | 0.341 | −35.95 (−111.00-39.11) | 176.18 (220.70) |
| Anti-SSA, IU/mL | 190.67 (41.64) | 206.51 (16.91) | 0.042 | −8.02 (−15.75-0.29) | 186.16 (52.59) |
| Anti-SSB, IU/mL | 71.38 (73.82) | 105.66 (97.50) | 0.145 | −18.77 (−44.22-6.68) | 71.32 (71.21) |

| | Week 24 | | | |
|---|---|---|---|---|
| | Placebo | p value | Difference (95% CI) | p value* |
| ESSPRI score change from baseline | −0.15 (0.18) | 0.002 | −0.80 (−1.3−−0.30) | 0.000 |
| ESSDAI score change from baseline | −0.36 (0.14) | 0.001 | −0.73 (−1.14−−0.33) | 0.001 |
| SF-36 score change from baseline | −0.98 (3.74) | 0.288 | 6.10 (−5.46-17.65) | 0.541 |
| MFI-20 score change from baseline | −0.11 (1.21) | 0.06 | −3.25 (−6.64-0.14) | 0.013 |
| Fatigue, n (%) | 17 (81.0%) | 0.033 | 4.25 (1.08-16.77) | 0.004 |
| Arthritis, n (%) | 5 (71.4%) | 0.622 | 2.50 (0.32-19.53) | 0.061 |
| Parotid gland swelling, n (%) | 2 (100.0%) | 0.100 | NA | 0.205 |
| Purpura, n (%) | 1 (100.0%) | 0.333 | NA | NA |
| Leukopenia, n (%) | 10 (100.0%) | 0.214 | 0.73 (0.51-1.04) | 0.000 |
| Thrombocytopenia, n (%) | 3 (42.9%) | 1.000 | 1.13 (0.11-11.60) | 0.141 |
| γ-G, % | 26.04 (3.65) | 0.490 | −0.60 (−2.33-1.13) | 0.869 |
| IgA, g/L | 3.65 (1.50) | 0.572 | −0.10 (−0.46-0.25) | 0.205 |
| IgG, g/L | 23.79 (5.56) | 0.155 | −1.44 (−3.43-0.56) | 0.095 |
| ESR, mm/hr | 30.93 (21.53) | 0.201 | −5.48 (−13.99-3.02) | 0.251 |
| C3, g/L | 0.97 (0.24) | 0.044 | −0.02 (−0.11-0.07) | 0.231 |
| C4, g/L | 0.18 (0.04) | 0.302 | 0.01 (−0.01-0.03) | 0.993 |
| RF, IU/mL | 217.69 (344.21) | 0.061 | −76.22 (−156.00-3.57) | 0.043 |
| Anti-SSA, IU/mL | 204.14 (17.64) | 0.187 | −13.92 (−34.84-6.99) | 0.095 |
| Anti-SSB, IU/mL | 104.15 (93.17) | 0.267 | −12.70 (−35.48-10.08) | 0.191 |

Immunological Responses after IL-2 Therapy in Human

In relation to Table 7, twenty-three patients consented to comprehensive immunological analysis, including enumeration of Treg and effector CD4+ T cell subsets (Th1, Th2, Th17 and T follicular helper (Tfh) cells). RhIL-2 therapy was associated with a significant expansion of Treg cells as a proportion of total CD4+ T cells (P<0.001) (see, FIGS. 2 A-E). Treg cell numbers changed in a way that suggested expansion during treatment, and contraction in the subsequent 2-week interval, suggesting that the rhIL-2 administration sustained Treg cell expansion only temporarily.

TABLE 7

Immune cells change in SLE patients with low-dose IL-2 treatment

| Variables | Baseline | Week 10 | Week 12 | Week 24 | P value (Week 0 vs 10) | P value (Week 0 vs 12) |
|---|---|---|---|---|---|---|
| CD4+ T cells (%) | | | | | | |
| IL-2, mean ± SD | 42.24 ± 10.78 | 43.04 ± 14.00 | 43.82 ± 14.70 | 42.70 ± 12.93 | 0.774 | 0.909 |
| Placebo, mean ± SD | 41.61 ± 11.24 | 38.99 ± 10.73 | 43.78 ± 10.72 | 39.32 ± 14.66 | 0.357 | 0.245 |
| Treg cells (%) | | | | | | |
| IL-2, mean ± SD | 12.88 ± 10.42 | 17.19 ± 8.47 | 14.19 ± 6.07 | 12.11 ± 6.27 | 0.016 | 0.465 |
| Placebo, mean ± SD | 11.00 ± 3.42 | 11.12 ± 4.31 | 10.69 ± 4.33 | 11.16 ± 4.69 | 0.748 | 0.423 |
| CD8+ T cells (%) | | | | | | |
| IL-2, mean ± SD | 46.79 ± 11.96 | 45.93 ± 12.99 | 45.57 ± 13.86 | 44.85 ± 12.72 | 0.500 | 0.852 |
| Placebo, mean ± SD | 47.79 ± 11.48 | 45.42 ± 17.38 | 46.00 ± 10.84 | 47.97 ± 14.08 | 0.684 | 0.661 |
| NK cells (%) | | | | | | |
| IL-2, mean ± SD | 6.22 ± 4.88 | 12.38 ± 8.40 | 10.49 ± 8.26 | 6.94 ± 4.40 | <0.001 | 0.021 |
| Placebo, mean ± SD | 5.96 ± 6.04 | 6.97 ± 6.35 | 5.74 ± 4.50 | 6.09 ± 4.93 | 0.172 | 0.558 |

TABLE 7-continued

Immune cells change in SLE patients with low-dose IL-2 treatment

| Variables | Baseline | Week 10 | Week 12 | Week 24 | P value (Week 0 vs 10) | P value (Week 0 vs 12) |
|---|---|---|---|---|---|---|
| $CD56^{bri}$ in NK cells (%) | | | | | | |
| IL-2, mean ± SD | 6.89 ± 4.49 | 10.57 ± 6.62 | 6.49 ± 4.07 | 6.63 ± 5.18 | <0.001 | 0.627 |
| Placebo, mean ± SD | 8.31 ± 7.33 | 6.88 ± 5.00 | 7.42 ± 5.68 | 8.46 ± 6.95 | 0.245 | 0.517 |
| $CD56^{dim}$ in NK cells (%) | | | | | | |
| IL-2, mean ± SD | 76.00 ± 9.76 | 68.27 ± 17.51 | 78.77 ± 9.48 | 77.44 ± 8.81 | 0.022 | 0.157 |
| Placebo, mean ± SD | 65.44 ± 22.22 | 71.14 ± 17.96 | 69.43 ± 20.07 | 67.17 ± 22.42 | 0.247 | 0.288 |

Figure 2B:
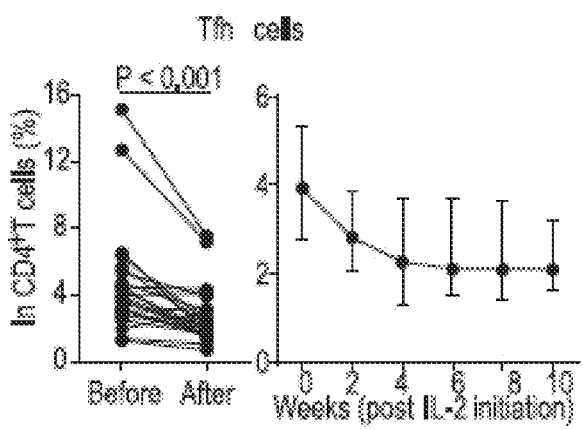
Figure 2C:
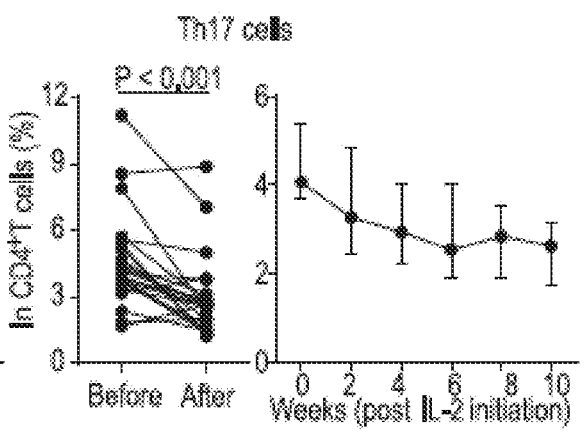
Figure 2D:
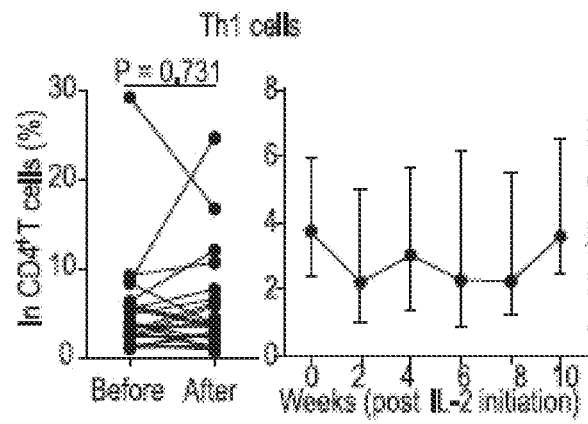
Figure 2E:
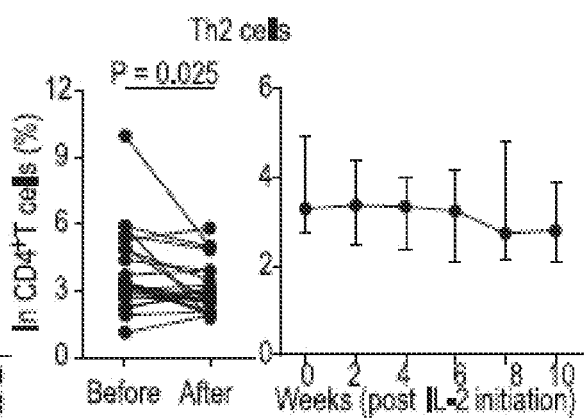
Figure 4A:
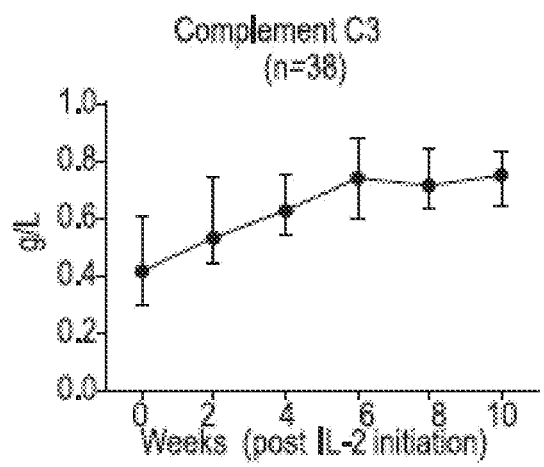
Figure 4B:
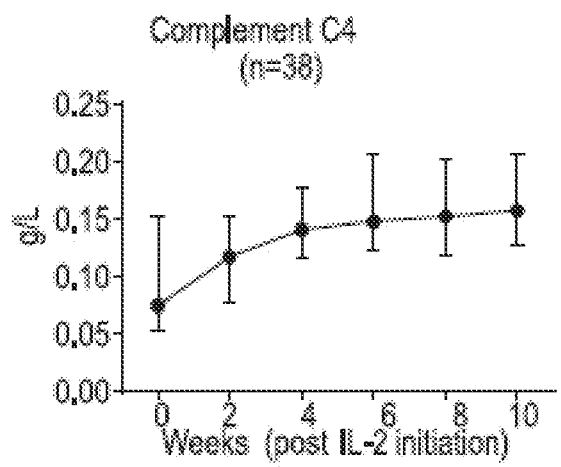
Figure 4C:
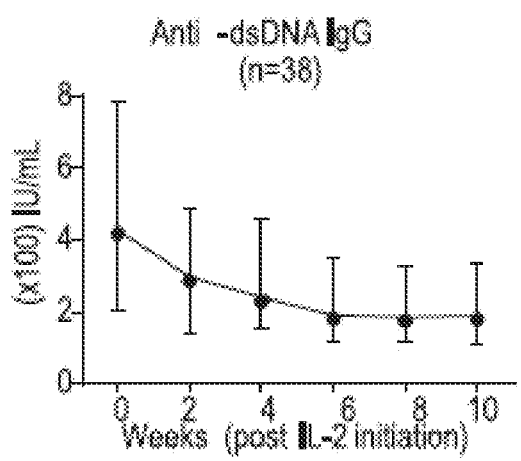
Figure 4D:
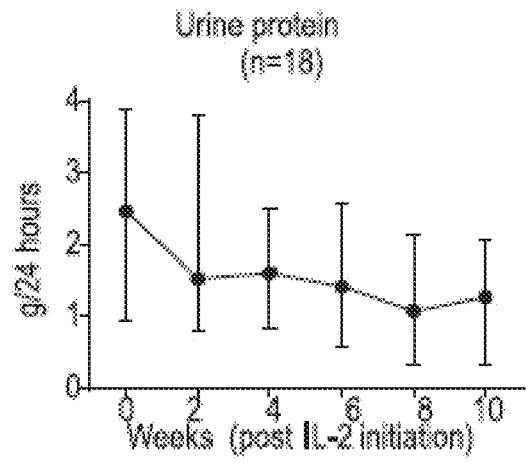
Figure 5A:
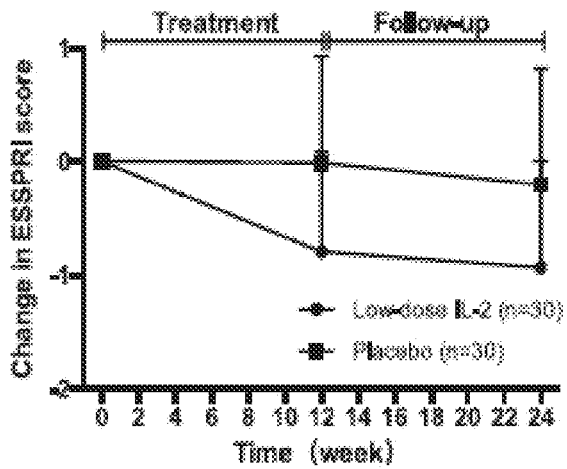
Figure 5B:
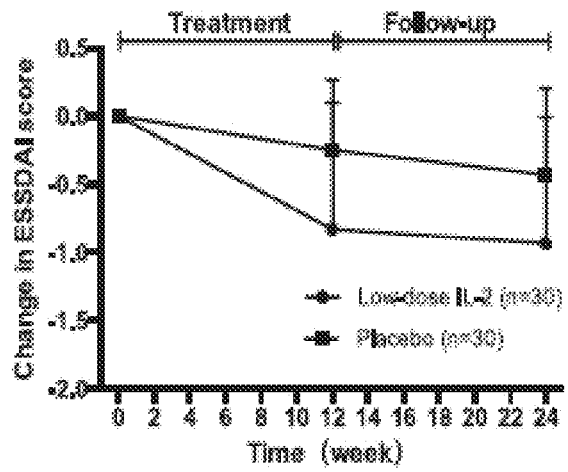
Figure 5C:
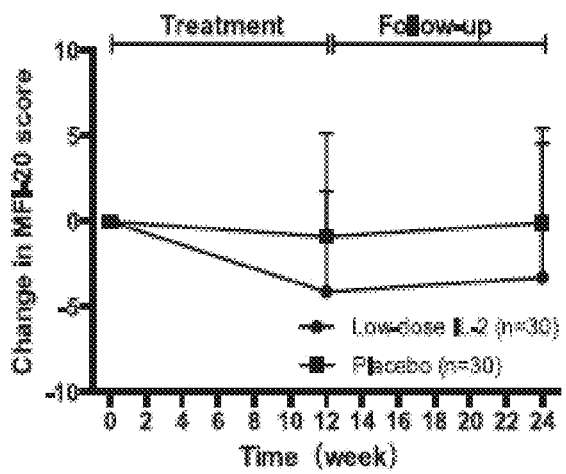
Figure 5D:
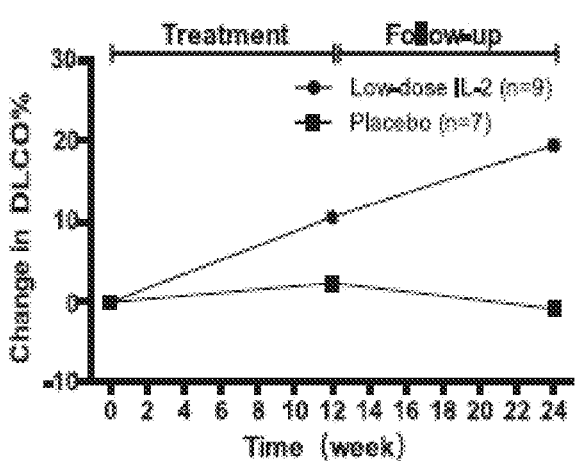
Figure 5E:
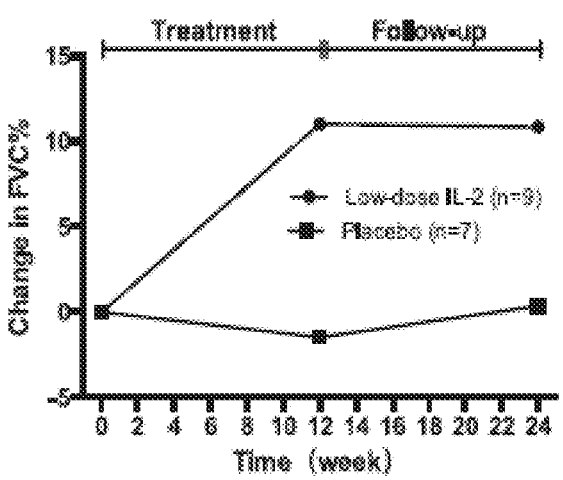
Figure 5F:
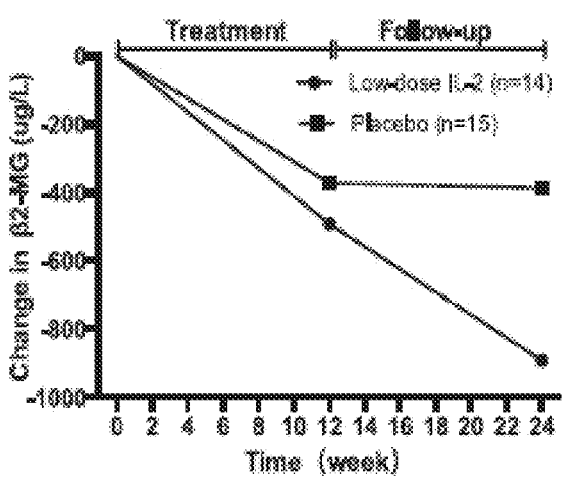
Figure 5G:
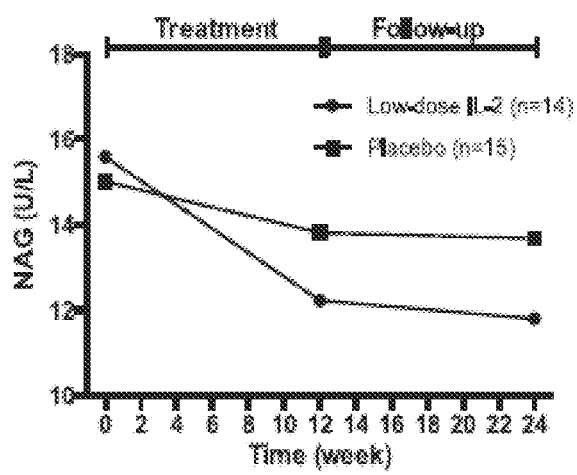
Figure 5H:
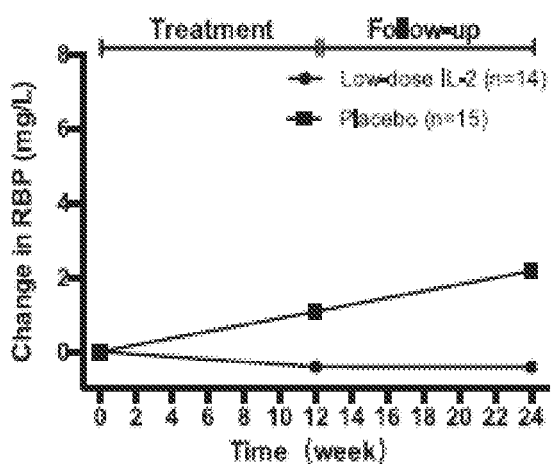
Figure 5I:
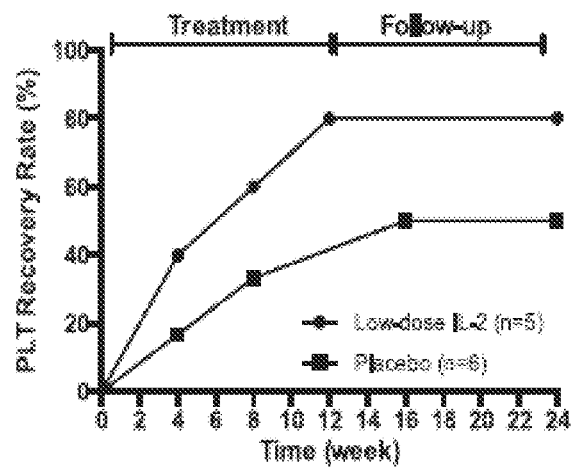
Figure 6A:
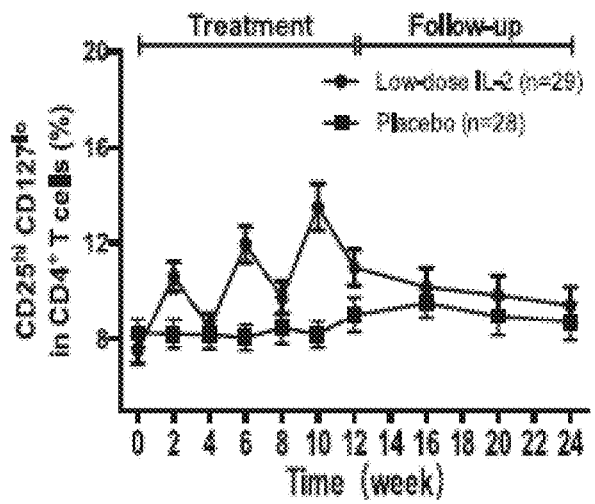
Figure 6B:
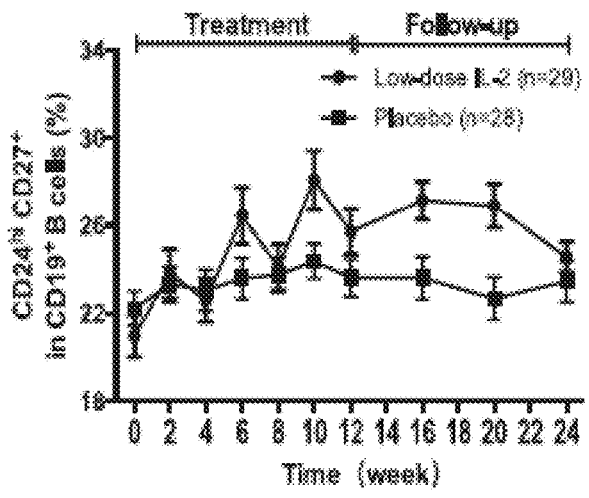
Figure 6C:
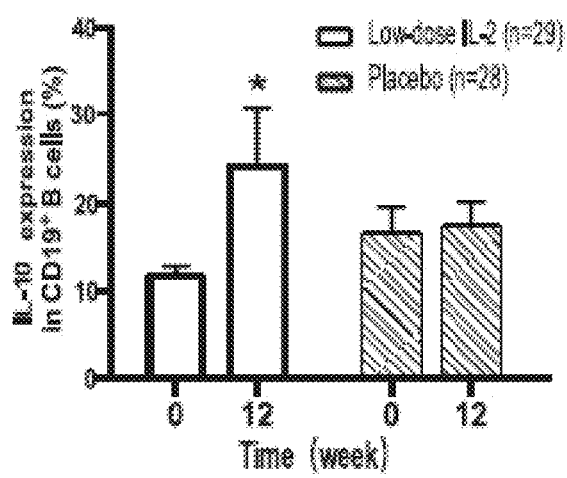
Figure 6D:
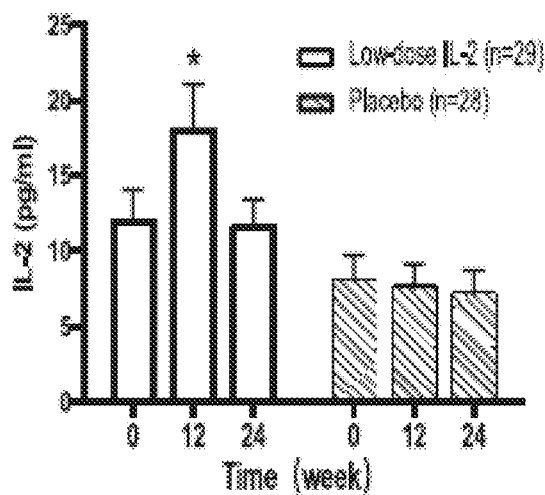
Figure 6E:
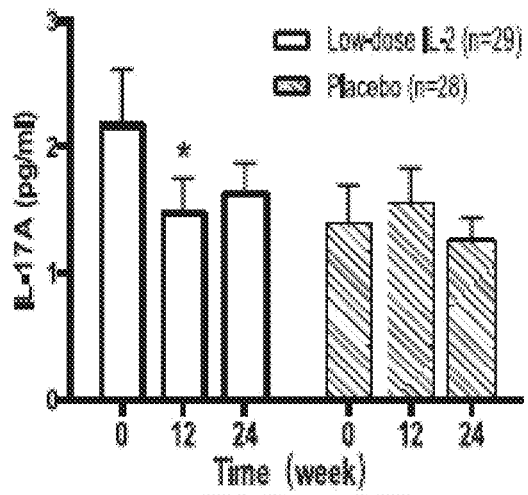
Figure 6F:
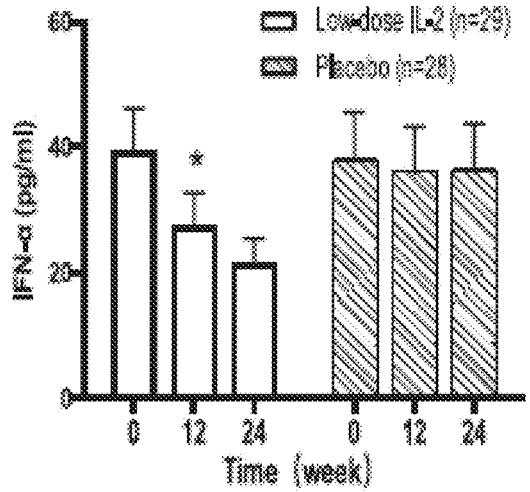
Figure 7A:
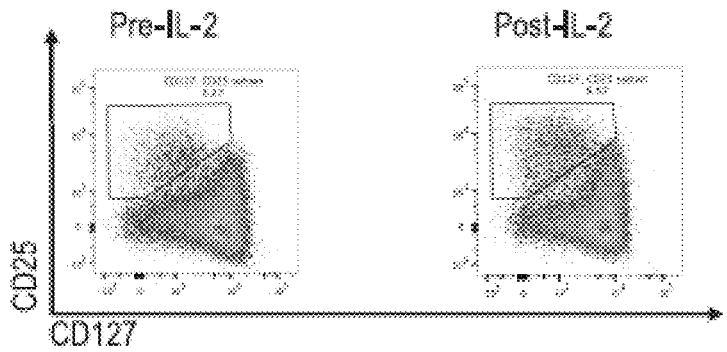
Figure 7B:
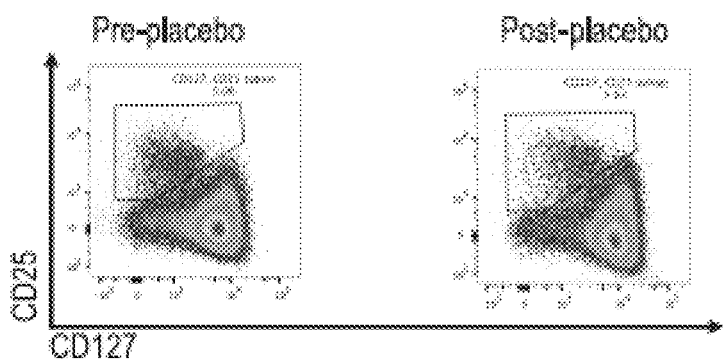
Figure 7C:
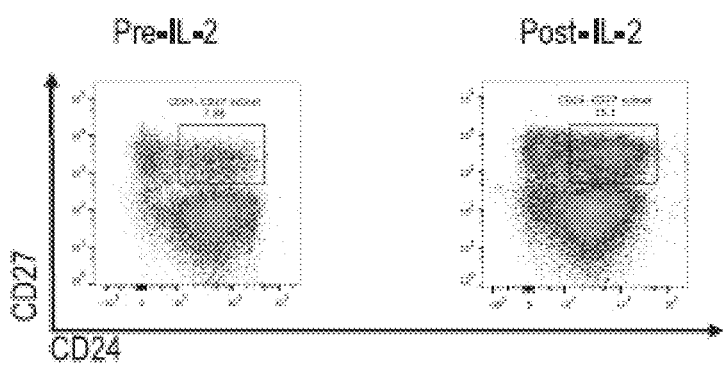
Figure 7D:
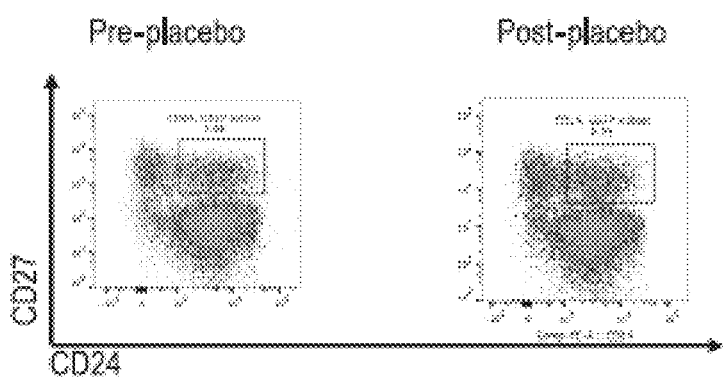
Figure 8A:
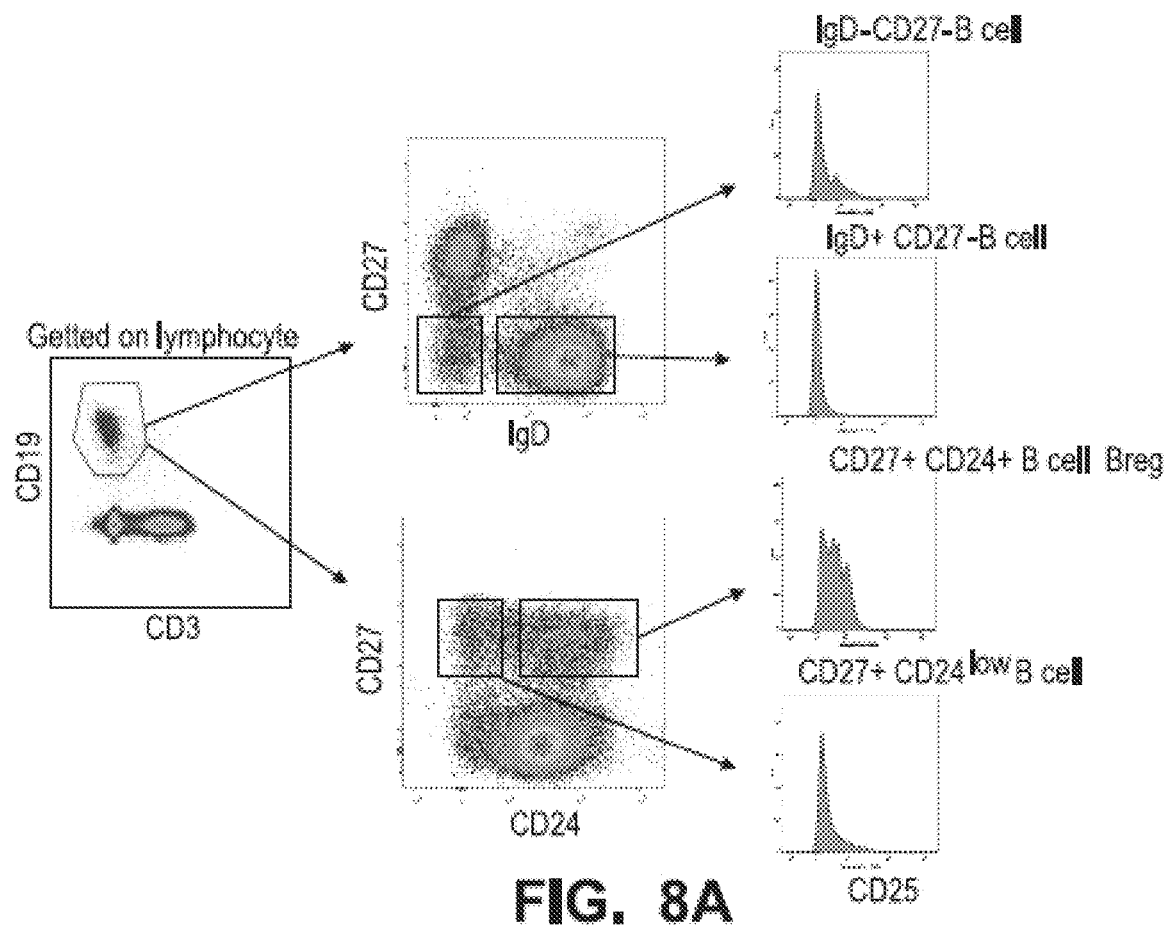
FIGS. 8A to 8B illustrate IL-2Rα expressing Breg cells gelled on lymphocyte for CD3:CD19; IgD:CD27; CD24: CD27 and the respective concentration graphs for FIG. 8A and the respective concentrations in relation to CD25 expression at FIG. 8B.
Figure 8B:
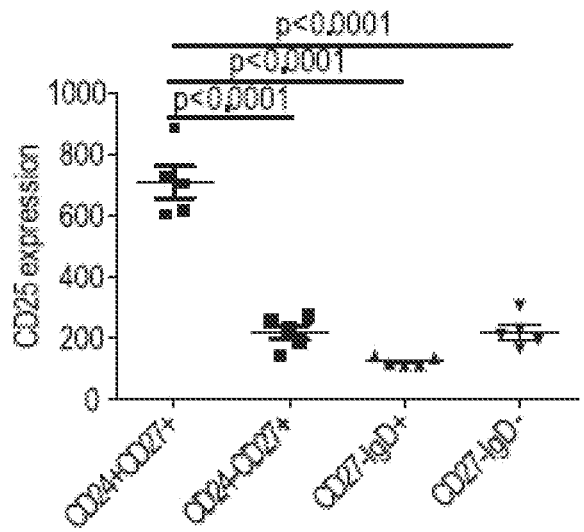
Figure 9A:
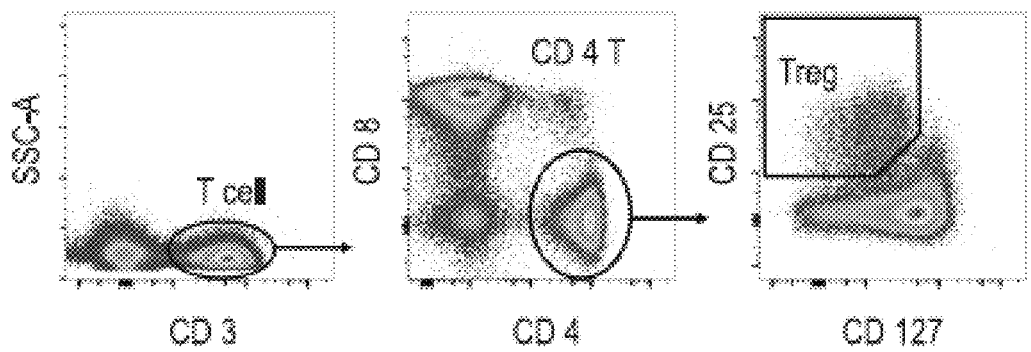
FIG. 9A to 9B illustrate, respectively, phentoyptic gating of T cells subsets and NK cell subsets. Natural Killer (NK) cells are lymphocytes in the same family as T and B cells, coming from a common progenitor. However, as cells of the innate immune system, NK cells are classified as group I Innate Lymphocytes (ILCs) and respond quickly to a wide variety of pathological challenges. NK cells are best known for killing virally infected cells and detecting and controlling early signs of cancer.
Figure 9B:
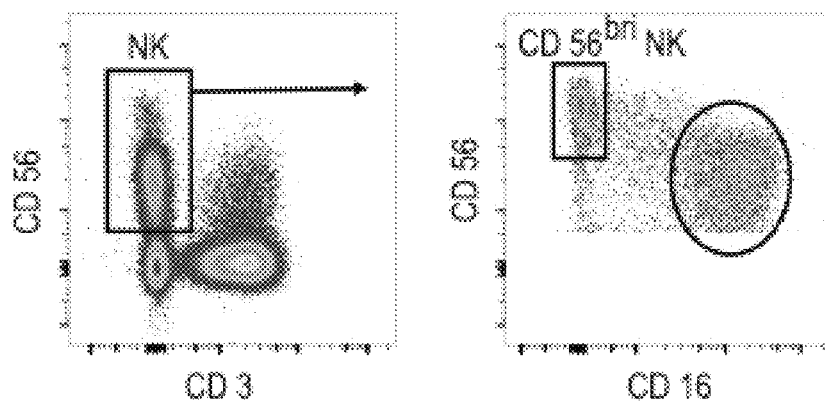
Figure 10A:
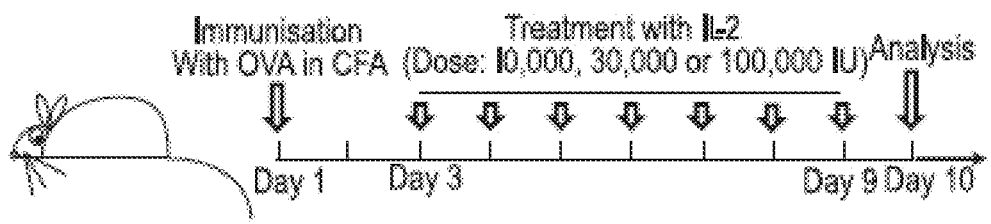
Figure 10B:
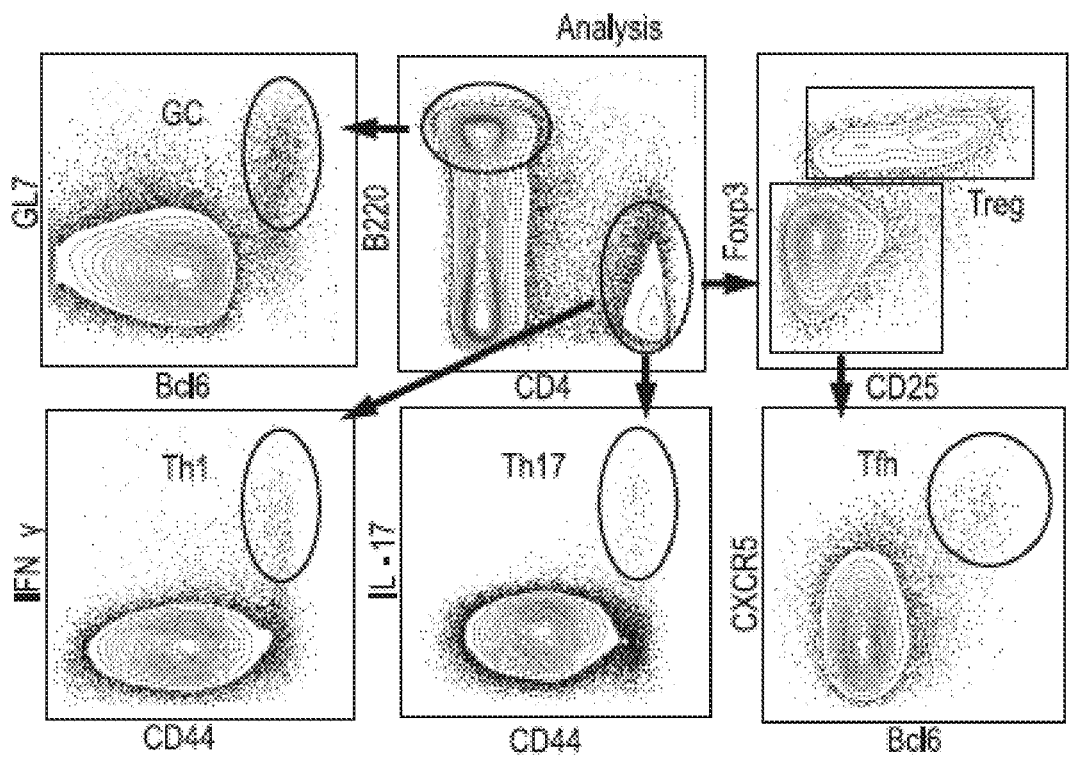
Figure 11A:
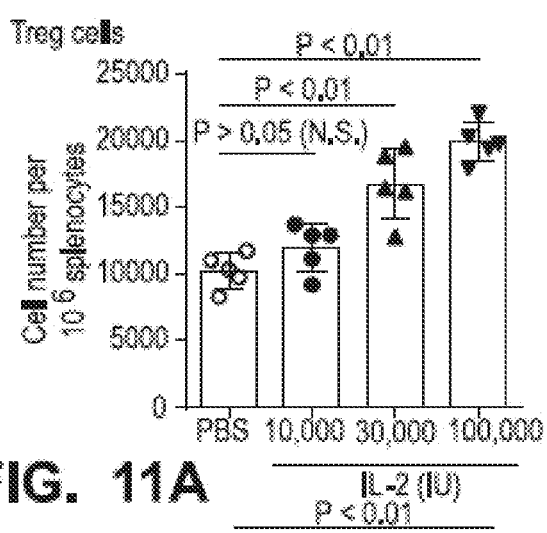
Figure 11B:
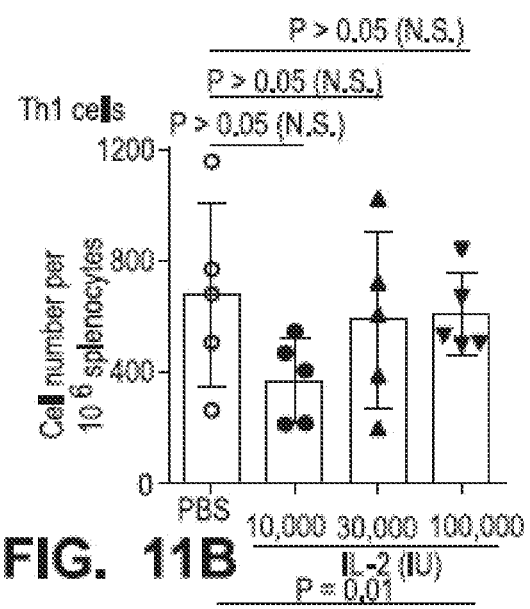
Figure 11C:
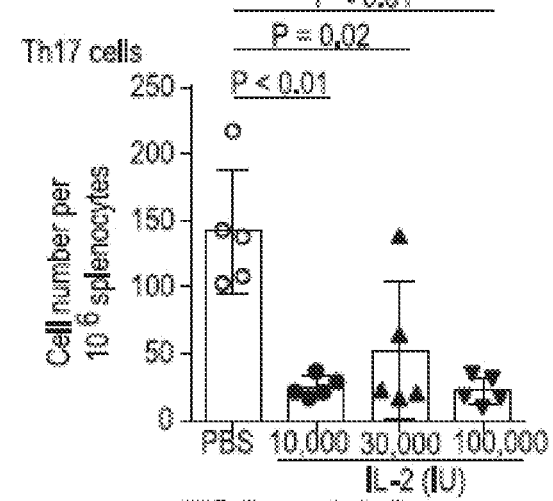
Figure 11D:
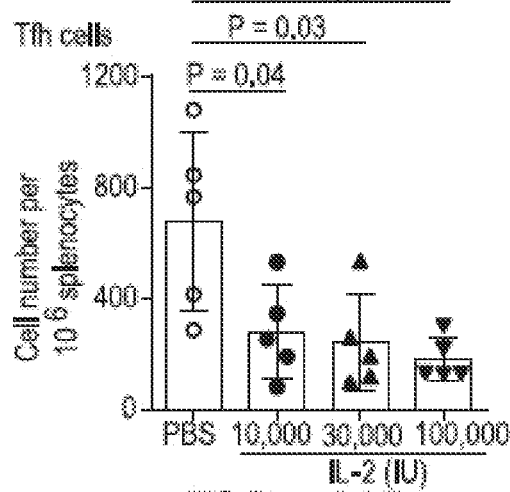
Figure 11E:
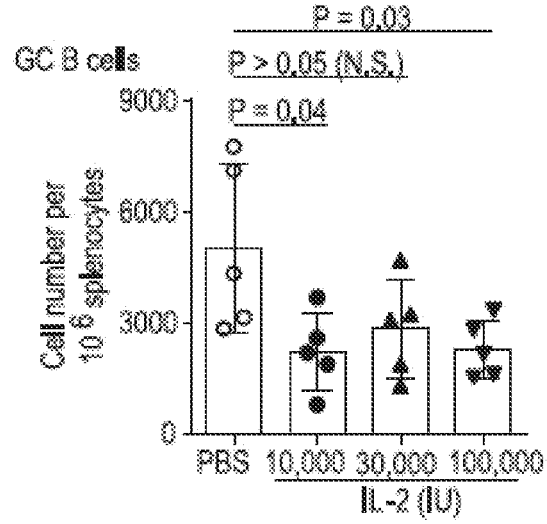

As illustrated at FIGS. 2B and C, effector Tfh and Th17 cells were significantly reduced in association with rhIL-2 administration. As a proportion of CD4+ T cells, Tfh cells reduced from a median of 3.93% (range, 1.27 to 15.14) to 1.99% (range, 0.69 to 7.55) (P<0.001); and Th17 cells from 4.08% (range, 1.69 to 11.18) to 2.67% (range, 1.28 to 8.87) (P=0.001). Similarly, mean serum IL-17A concentrations were lower after 12 weeks of rhIL-2 treatment than at baseline, although reductions were not observed in all patients (data not shown). However, the proportions of two other major conventional CD4+ T cell subsets, namely Th1 and Th2 cells, were largely unaltered by the IL-2 therapy (see. FIGS. 2D and 2E). Observations were performed and confirmed a significant reduction of CD4-CD8-αβ (double negative, DN) T cells in response to low-dose rhIL-2 (see, FIGS. 3A to 3I in relation to FIG. 2B).

Immune Response

IL-2 treatment induced the expansion of Treg cell during treatment, which contracted in the subsequent 2-week interval (see, FIG. 3A, Table 8). In addition, we found that IL-2 treatment also induced significant expansion of B10 cells—B cells are commonly thought to enhance inflammatory immune responses, however, specific regulatory B cell subsets were identified that downregulate adaptive and innate immunity, inflammation, and autoimmunity through diverse molecular mechanisms; that said, in both mice and humans, a rare, but specific, subset of regulatory B cells is functionally characterized by its capacity to produce IL-10, a potent inhibitory cytokine; this regulatory B cell subset has been labeled as B10 cells, because their ability to downregulate immune responses and inflammatory disease is fully attributable to IL-10, and their absence or loss exacerbates disease symptoms in mouse models—expressing CD25. The serum IL-2 levels were increased with IL-2 treatment, and there was a significant reduction of pro-inflammatory cytokines such as IL-17A and IFN-α in patients in the IL-2 group (see, FIGS. 3D, 3E and 3F and Table 8). Collectively, low-dose IL-2 therapy reinstated immune balance in patients with primary Sjögren's Syndrome (pSS) by potentiating immunoregulatory cells while attenuating the pro-inflammatory cytokine milieu.

TABLE 8

Phenotype change of NK cells in SLE patients

| Variables | Baseline | Post Treatment | P value |
|---|---|---|---|
| IFN-γ+ NK cells (%) | | | |
| IL-2, mean ± SD | 68.92 ± 16.92 | 82.81 ± 12.22 | 0.024 |
| Standard treatment, mean ± SD | 65.76 ± 14.46 | 73.51 ± 17.26 | 0.254 |
| NKp46+ NK cells (%) | | | |
| IL-2, mean ± SD | 92.68 ± 4.40 | 96.87 ± 2.71 | 0.025 |
| Standard treatment, mean ± SD | 92.11 ± 6.56 | 94.07 ± 6.85 | 0.562 |
| NKG2D+ NK cells (%) | | | |
| IL-2, mean ± SD | 83.84 ± 4.47 | 91.11 ± 6.14 | 0.003 |
| Standard treatment, mean ± SD | 88.46 ± 6.18 | 88.02 ± 6.92 | 0.748 |

* IL-2 group (n = 10); standard treatment group (n = 10).

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

1. Sanofi-Aventis. Product monograph: Plaquenil. http://products.sanofi.ca/en/plauenil.pdf. Feb. 5, 2019.
2. Centers for Disease Control and Prevention (CDC). Malaria information and prophylaxis, by country. www.cdc.gov/malaria/travelers/country_table/a.html. Accessed May 2, 2018.
3. Wallace D J. The history of antimalarials. Lupus 1996; 5(suppl 1):S2-S3. pmid:8803902
4. Shee J C. Lupus erythematosus treated with chloroquine. Lancet 1953; 265(6778):201-202. pmid: 13070595
5. Kuznik A, Bencina M, Svajger U, Jeras M, Rozman B, Jerala R. Mechanism of endosomal TLR inhibition by antimalarial drugs and imidazoquinolines. J Immunol 2011; 186:4794-4804. doi:10.4049/jimmunol. 1000702
6. Willis R, Seif A M, McGwin G Jr, et al. Effect of hydroxychloroquine treatment on pro-inflammatory cytokines and disease activity in SLE patients: data from LUMINA, a multiethnic US cohort. Lupus 2012; 21(8): 830-835. doi:10.1177/0961203312437270
7. Fox R. Anti-malarial drugs: possible mechanisms of action in autoimmune disease and prospects for drug development. Lupus 1996; 5(suppl 1):S4-S10. pmid: 8803903
8. Ruiz-Irastorza G, Ramos-Casals M, Brito-Zeron P, Khamashta M A. Clinical efficacy and side effects of antimalarials in systemic lupus erythematosus: a systematic review. Ann Rheum Dis 2010; 69(1):20-28. doi: 10.1136/ard.2008.101766
9. Lam N C, Ghetu M V, Bieniek M L. Systemic lupus erythematosus: primary care approach to diagnosis and management. Am Fam Physician 2016; 94(4):284-294. pmid:27548593

10. Jung H, Bobba R, Su J, et al. The protective effect of antimalarial drugs on thrombovascular events in systemic lupus erythematosus. Arthritis Rheum 2010; 62(3):863-868. doi: 10.1002/art.27289
11. Gottenberg J E, Ravaud P, Puechal X, et al. Effects of hydroxychloroquine on symptomatic improvement in primary Sjogren syndrome. JAMA 2014; 312(3):249-258. doi:10.1001/jama.2014.7682

We claim:

1. A method of inhibiting or treating systemic lupus erythematosus (SLE) in a subject in need thereof, the method consisting of administering to the subject a therapeutically effective low-dose amount of interleukin-2 in combination with a therapeutically effective amount of hydroxychloroquine, thereby inhibiting or treating SLE in the subject.

2. The method of claim 1, wherein said administering is administering no more than 24 weeks.

3. The method of claim 2, wherein said administering is administering no more than 12 weeks.

4. The method of claim 1, wherein the subject is a human.

5. The method of claim 1, wherein the low-dose of interleukin-2 is 0.1 MIU/day to 3.5 MIU/day.

6. The method of claim 1, wherein the low-dose of interleukin-2 is 0.1 MIU/every other day to 3.5 MIU/every other day.

7. A method of inhibiting or treating primary Sjogren's syndrome (pSS) in a subject in need thereof, the method consisting of administering to the subject a therapeutically effective low-dose amount of interleukin-2 in combination with a therapeutically effective amount of hydroxychloroquine, thereby inhibiting or treating pSS in the subject.

8. The method of claim 7, wherein said administering is administering no more than 24 weeks.

9. The method of claim 8, wherein said administering is administering no more than 12 weeks.

10. The method of claim 7, wherein the subject s a human.

11. The method of claim 7, wherein the low-dose of interleukin-2 is 0.1 MIU/day to 3.5 MIU/day.

12. The method of claim 7, wherein the low-dose of interleukin-2 is 0.1 MIU/every other day to 3.5 MIU/every other day.

* * * * *